United States Patent
Vadas et al.

(12)

(10) Patent No.: US 6,322,791 B1
(45) Date of Patent: Nov. 27, 2001

(54) HAEMOPOIETIC GROWTH FACTOR ANTAGONISTS AND USES THEREFOR

(75) Inventors: Mathew Alexander Vadas, Stirling; Angel Francisco Lopez, North Adelaide; Mary Francis Shannon, Crafers; Keat-Chye Cheah, Aberfoyle Park; Carol Ruth Senn, Forest Range; Stan Bastiras, Adelaide; Allan Robins, Waterloo Corner, all of (AU)

(73) Assignee: BreasaGen Limited, Adelaide (AU)

( * ) Notice: Subject to any disclaimer, the term of this patent is extended or adjusted under 35 U.S.C. 154(b) by 0 days.

(21) Appl. No.: 08/983,523

(22) PCT Filed: Jun. 21, 1996

(86) PCT No.: PCT/AU96/00382

§ 371 Date: May 28, 1998

§ 102(e) Date: May 28, 1998

(87) PCT Pub. No.: WO97/00695

PCT Pub. Date: Jan. 9, 1997

Related U.S. Application Data

(63) Continuation-in-part of application No. 08/591,438, filed on Aug. 17, 1999, now Pat. No. 5,939,063.

(30) Foreign Application Priority Data

Jun. 23, 1995 (AU) .................................................. PN 3780

(51) Int. Cl.[7] .......................... A61K 39/00; A61K 45/00; A61K 38/00; A61K 38/18
(52) U.S. Cl. .......................... 424/198.1; 424/85.1; 514/2; 530/399; 530/324; 530/351
(58) Field of Search ................................. 424/85.1, 198.1; 530/324, 351, 399

(56) References Cited

U.S. PATENT DOCUMENTS 5,475,087  * 12/1995  Seelig et al. ........................ 530/326
5,795,966  *  8/1998  Grabstein ......................... 530/388.23

FOREIGN PATENT DOCUMENTS

| 0409091A1 | 1/1991 | (EP) . |
| 0499161A2 | 8/1992 | (EP) . |
| WO89/10403 | 11/1989 | (WO) . |
| WO89/11864 | 12/1989 | (WO) . |
| WO91/10684 | 7/1991 | (WO) . |
| WO95/04075 | 2/1995 | (WO) . |

OTHER PUBLICATIONS

Kinoshita, et al.; The EMBO Journa; vol. 14, No. 2, pp. 266–275; 1995; Suppression of apoptotic death in hematopoietic cells by signalling through the IL–3/GM–CSF receptors.

Han, et al.; Experimental Hematology 23: 265–272 (1995); Modulation of apoptosis in human myeloid leukemic cells by GM–CSF.

Bach, et al.; Pathogenesis; Int Arch Allergy Immunol 1995; 107: 90–92; Evidence that Granuocyty/Macrophage–Colony–Stimulating Factor and Interferon–Maintain the Viability of Human Peripheral Blood Monocytes in Part by their Suppression of Il–10 Production.

Iversen, et al.; Proc.Natl.Acad.Sci.USA; vol. 93, pp. 2785–2789; Apr. 1996; Apoptosis of hemopoietic cells by the human granulocyte–macrophage colony–stimulating factor mutant E21r.

* cited by examiner

Primary Examiner—Yvonne Eyler
Assistant Examiner—Janet L. Andres
(74) Attorney, Agent, or Firm—Knobbe, Martens, Olson & Bear LLP

(57) ABSTRACT

The present invention relates generally to variant recombinant forms of haemopoietic growth factors useful as antagonists to the corresponding native haemopoietic growth factor and their use in ameliorating aberrant effects caused by the native molecules and in the treatment of tumours and cancers and inflammation.

17 Claims, 16 Drawing Sheets

HAEMOPOIETIC GROWTH FACTOR ANTAGONISTS AND USES THEREFOR

Figure 1:
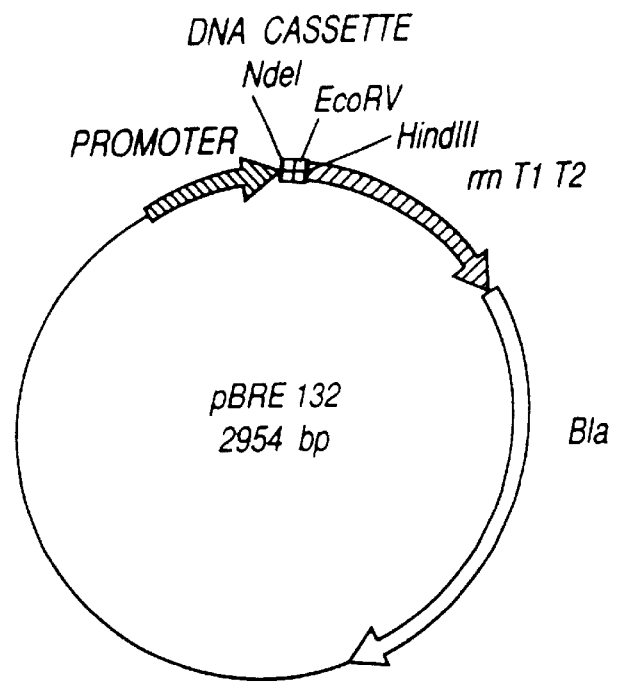

This is a Continuation in Part of U.S. Pat. No. 5,939,063, issued Aug. 17, 1999, and is the U.S. National phase under 35 U.S.C §371 of International Application PCT AU96/00382, filed Jul. 28, 1999.

The present invention relates generally to variant recombinant forms of haemopoietic growth factors useful as antagonists to the corresponding native haemopoietic growth factor and their use in ameliorating aberrant effects caused by the native molecules and in the treatment of tumours and cancers and inflammation.

Sequence Identity Numbers (SEQ ID NOs.) for the nucleotide and amino acid sequences referred to in the specification are defined following the description.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The rapidly increasing sophistication of recombinant DNA technology is greatly facilitating research and development in a range of industries. The medical and allied health fields in particular have, and continue to, benefit from this developing technology. An area of substantial interest is the field of growth factors and cytokines.

Granulocyte-macrophage colony-stimulating factor (GM-CSF) is one member of a family of haemopoietic growth factors (HGFs) and exhibits a range of important activities such as supporting survival of normal leukaemic and haemopoietic cells by suppressing programmed cell death, which is also known as apoptosis. GM-CSF binds to a heterodimeric receptor composed of a GM-CSF specific α chain and a βc chain which is shared with the receptors for interleukins (IL) 3 and 5. Both chains are required for GM-CSF mediated signaling.

In International Patent Application No. PCT/AU94/00432 filed on Jul. 28, 1994, which is incorporated herein by reference, a series of HGF antagonists was described. It has now been surprisingly discovered that certain forms or types of these antagonists induce apoptosis in cells expressing HGF receptors. This property of the HGF antagonists provides inter alia a novel approach to the treatment of a range of tumours and cancers and in particular myeloid leukaemias.

Accordingly, one aspect of the present invention contemplates a method for inducing apoptosis in cells carrying an HGF heterodimeric receptor comprising an HGF-specific α-chain and a βc chain, said method comprising contacting said cells with an effective amount of an HGF antagonist for a time and under conditions sufficient to induce apoptosis wherein said HGF antagonist comprises a sequence of amino acids within a first α-helix of HGF wherein one or more exposed amino acids in said first α-helix of HGF having acidic properties is/are substituted with a basic amino acid residue or a non-acidic amino acid residue.

The HGFs are preferably GM-CSF, IL-2, IL-3, IL-4, IL-5, IL-6, IL-7, IL-9, IL-10, EL-11, IL-13, IL-14, IL-15 and others of this family yet to be discovered, granulocyte colony-stimulating factor (G-CSF), erythropoietin (EPO) and thrombopoietin (TPO). Most preferably, the HGF is GM-CSF.

According to this aspect of the present invention there is provided a method for inducing apoptosis in cells carrying an HGF heterodimeric receptor comprising an HGF-specific α-chain and a βc chain, said method comprising contacting said cells with an effective amount of an GM-CSF antagonist for a time and under conditions sufficient to induce apoptosis wherein said GM-CSF antagonist comprises a sequence of amino acids within a first α-helix of HGF wherein one or more exposed amino acids in said first α-helix of HGF having acidic properties is/are substituted with a basic amino acid residue or a non-acidic amino acid residue.

The HGF antagonists are preferably produced in recombinant or synthetic form and, with the exception of the amino acid substitution(s) in the first α-helix, the amino acid sequence of the HGF may be the same as the naturally occurring molecule (i.e. native molecule) or may carry single or multiple amino acid substitutions, deletions and/or additions to the native sequence.

In one particular embodiment, the HGF antagonists are:
(i) in unglycosylated form;
(ii) lack post-translational modification;
(iii) produced in prokaryotic microorganisms; and/or
(iv) produced by chemical synthesis.

The antagonists may be derivatives of an HGF or may be any other molecule which selectively binds to the α-chain of the HGF receptor such as, but not limited to, antibodies or other small or large molecules resulting in apoptosis. The present invention is hereinafter described with reference to GM-CSF antagonists and in particular human GM-CSF antagonists or mammalian GM-CSF antagonists capable of functioning in humans. This is done, however, with the understanding that the present invention extends to any HGF antagonist which is capable of inducing cell apoptosis by interaction with an HGF-specific α-chain of an HGF receptor. The present invention also extends to HGF antagonists which interact with the β chain.

Although not intending to limit the present invention to any one theory or mode of action, it is proposed that the GM-CSF antagonist either blocks the action of wild-type GM-CSF by interacting selectively with the receptor α-chain or induces apoptosis by interacting with the α- and β-chains of the receptor in a manner that leads to abnormal stimulation of the β-chain either qualitatively or quantitatively. Qualitative differences to wild-type GM-CSF include recruitment of signalling molecules (for example, type of kinase or state); quantitative differences include intensity of duration of signalling.

The present invention is particularly directed to the use of a GM-CSF antagonist carrying a substitution of amino acid 21 (Glu) of human GM-CSF by Arg or Lys or any other basic or non-acidic amino acid residue. Such mutants are designated herein "E21R" and "E21K", respectively, which is based on a single letter designation of the amino acids involved in the substitution and the position of the substitution. The construction of vectors expressing E21R is described in the Examples. E21R is a fusion protein expressed in inclusion bodies as GM-CSF(E21R) preceded by a twelve amino acid leader sequence, namely, MFATSSSTGNDG (SEQ ID NO:3)

In accordance with the present invention, it has been surprisingly discovered that GM-CSF antagonist E21R binds to the GM-CSF-specific α-chain of the GM-CSF receptor and that such binding directly induces apoptosis of normal and malignant myeloid cells expressing the GM-CSF receptor. Apoptosis occurs even in the presence of the survival factors such as G-CSF and stem cell factor (SCF) but is prevented by engaging receptor chain βc with IL-3.

Accordingly, in a particularly preferred embodiment, the present invention contemplates a method for inducing apoptosis of myeloid cells said method comprising contacting said cells with an apoptotic effective amount of a GM-CSF antagonist having a basic amino acid residue substituted at position 21 of the GM-CSF amino acid sequence for a time and under conditions sufficient for programmed cell death to initiate.

This method has particular relevance in the treatment of cancers such as myeloid leukaemias and inflammation, for example, rheumatoid arthritis and allergic conditions such as asthma. Preferred GM-CSF antagonists comprise amino acids Arg or Lys at position 21 of GM-CSF. The most preferred antagonist comprises Arg at position 21 of GM-CSF and is referred to herein as E21R.

Accordingly, a further aspect of the present invention contemplates a method of inducing apoptosis in a cell carrying receptors for GM-CSF, said method comprising contacting said cell with a molecule capable of binding to the α-chain of the GM-CSF receptor or binding both to the α-chain and β-chain for a time and under conditions sufficient for programmed cell death to initiate.

Preferably, the molecule is a derivative of GM-CSF with amino residue 21 substituted by a basic amino acid.

Preferably, the basic amino acid residue is Arg or Lys. Most preferably, the basic amino acid residue is Arg.

Preferably, the molecules are:

(i) in unglycosylated form;

(ii) lack post-translational modification;

(iii) produced in prokaryotic microorganisms; and/or (iv) produced by chemical synthesis.

Another aspect of the present invention contemplates a method for treating myeloid leukaemia in a human subject, said method comprising administering to said human subject an effective amount of an HGF antagonist, said administration being for a time and under conditions sufficient to induce apoptosis of said myeloid leukaemic cells wherein said HGF antagonist comprises a sequence of amino acids within a first α-helix of HGF wherein one or more exposed amino acids in said first α-helix having acidic properties is/are substituted with a basic amino acid residue or a non-acidic amino acid residue.

Preferably, the HGF receptor is a GM-CSF receptor.

Preferably, the HGF antagonist is a GM-CSF antagonist.

Preferably, the GM-CSF antagonist comprises Arg or Lys at position 21 of the GM-CSF amino acid sequence.

Preferably, the GM-CSF antagonist is E12R.

Induction of apoptosis will also be useful in enrichment of uncommitted progenitors for stem cell transplantation and gene transfer purposes. According to this aspect of the present invention there is provided a method for enriching uncommitted progenitor cells from bone marrow said method comprising contacting a population of cells from bone marrow with an effective amount of a molecule capable of stimulating the α-chain of an HGF receptor or abnormally stimulating the βc chain of said receptor for a time and under conditions sufficient to induce apoptosis of cells carrying said α-chain.

Preferably, the molecule is a derivative of an HGF having a sequence of amino acids within a first α-helix wherein one or more exposed amino acids in said first α-helix having acidic or acidic-like properties are substituted with a basic amino acid residue or non-acidic amino acid residue.

Preferably, the molecule is a derivative of GM-CSF, IL-2, IL-3, IL-4, IL-5, IL-6, IL-7, IL-9, IL-10, IL-11, IL-13, IL-14, IL-15 and others of this family yet to be discovered, 6-CSF, EPO or TPO.

Preferably, the molecule is GM-CSF having Arg or Lys at position 21 in place of Glu.

Most preferably, the molecule is E21R.

Preferably, apoptosis occurs with committed progenitors ($CD34^+$ $CD\mathbf{38}^+$, $CD34^+$ $CD33^+$) but not $CD34^+$ $CD38^-$cells.

The present invention further contemplates genetic constructs useful in expressing E21R including constructs comprising the nucleotide sequence encoding the leader sequence MFATSSSTGNDG(SEQ ID NO:3).

The present invention also contemplates a method for purifying E21R with or without the leader sequence following expression of the above-mentioned genetic constructs.

Yet a further aspect of the present invention contemplates eukaryotic or prokaryotic organisms carrying the above-mentioned genetic constructs.

Preferred aspects of these embodiments are described in the Examples.

The present invention is further described by reference to the following non-limiting Figures and Examples.

In the Figures:

FIG. 1 is a schematic representation of plasmid pBRE132. The DNA cassette has a unique EcoRV cloning site and codes for MFATSSSTGND (SEQ ID NO:3) leader sequence.

FIG. 2 is a schematic representation of plasmid pBRE133. SmaI/HindII GM-321R PCR DNA was cloned into EcoR-ViHindIII sites of pBRE132. PBRE133 encodes MFATSSSTGNDG-GM-CSF protein (designated herein "E21R" SEQ ID NO:3).

FIG. 3 is a graphical representation showing competition of binding of E21R and 1 nM $^{125}$I-GM-CSF to CHO cells transfected with GMRα (GM-CSF-specific α-chain of GM-CSF receptor).

FIG. 4 is a graphical representation showing antagonism of GM-CSF by E21R in a human erythroleukaemia cell line TF1 proliferation assay.

FIG. 5 is a graphical representation showing antagonism of GM-CSF by E21R in a neutrophil superoxide assay.

FIG. 6 is a graphical representation showing that E21R inhibits GM-CSF stimulated proliferation of AML cells.

FIG. 7 is a graphical representation showing that E21R inhibits GM-CSF stimulated proliferation of CML cells.

FIG. 8 is a graphical representation showing that E21R inhibits colony growth of JCML cells.

FIG. 9 is a photographic representation showing that the E21R causes DNA fragmentation in myeloid cells. FIG. 9 is a photographic representation showing that the E21R causes DNA fragmentation in the following myeloid cells: Top left panel: Myeloid leukemia cells expressing the GM-CSF-specific α-chain of the GM-CSF receptor, from a patient suffering acute myeloid leukemia (AML/$GMR\alpha^+$ cells); Top right panel: Normal bone marrow cells expressing CD34 and the GM-CSF-specific α-chain of the GM-CSF receptor (BM $CD34^+/GMR\alpha^+$ cells); Middle left panel: Normal bone marrow cells expressing CD34, CD38, and the GM-CSF-specific α-chain of the GM-CSF receptor (BM $CD34^+$ $CD38^+/GMR\alpha^+$ cells); Middle right panel: Normal bone marrow cells expressing CD34, but not expressing CD38, or the GM-CSF-specific α-chain of the GM-CSF receptor (BM $CD34^+CD38^-/GMR\alpha^-$ cells); and Lower panel: Normal bone marrow cells expressing CD34, CD33, and the GM-CSF-specific α-chain of the GM-CSF receptor (BM $CD34^+$ $CD33^+/GMR\alpha^+$ cells). Cells were incubated in the presence of either medium alone (lane 2 in each panel labeled "medium"), wild-type GM-CSF protein (lane 3 in each panel labeled "GM-CSF"), or GM-CSF E21R protein (lane 4 in each panel labeled "E21R"). DNA size (kb) for each sample was estimated by comparison to a known standard (lane 1 in each panel labeled "Marker (kb)"), for which the lengths are indicated at the left side of the top and middle panels. DNA extracts from cells were electrophoresed on agarose gels under standard conditions and visualized under ultraviolet light following staining with ethidium bromide. Lower molecular weight DNA was only observed in extracts of cells having the GM-CSF-specific α-chain of the GM-CSF receptor that were incubated with GM-CSF E21R.

FIG. 10 are graphical representations showing that E21R induces apoptosis of GMRα$^+$ myeloid leukaemic cells in a time- and dose-dependent manner.

FIG. 10*a* is a graphical representation showing the DNA content (abscissa) and number of nuclei (ordinate) of myeloid leukemia cells expressing the GM-CSF-specific α-chain of the GM-CSF receptor, from a patient suffering acute myeloid leukemia (i.e. AML/GMRα$^+$ cells) at 24 hours (left panel), 36 hours (middle panel), and 48 hours (right panel) following incubation of cells with GM-CSF E21R protein. Data in left panel show characteristic peaks for cells in G0/G1-phase, S-phase, and G2/M-phase of cell division, 24 hours after addition of Gm-CSF E21R protein. Data in right and middle panels show increasing amounts of a broad peak of degraded DNA representative of apoptosis (Ap peak in middle and right panels), during prolonged incubation of cells with GM-CSF E21R protein. Error bars show the standard error of the mean.

FIG. 10*b* is a graphical representation showing the percentage of apoptotic AML/GMRα$^+$ cells as estimated from propidium iodide staining of DNA, following incubation of cells, for up to 48 hours, with medium alone (■), wild-type GM-CSF protein (●), or GM-CSF E21R protein (▲). Significant increases in numbers of apoptotic cells occurred following incubation of cells with GM-CSF E21R protein for 24 to 48 hours. Error bars show the standard error of the mean.

FIG. 10*c* is a graphical representation showing the percentage of apoptotic cells from a patient suffering chronic myeloid leukemia (i.e. CML/GMRα$^+$ cells) as estimated from propidium iodide staining of DNA, following incubation of cells, for up to 48 hours, with medium alone (■, wild-type GM-CSF protein (●), or GM-CSF E21R protein (▲). Significant increases in numbers of apoptotic cells occurred following incubation of cells with GM-CSF E21R protein for 24 to 48 hours. Error bars show the standard error of the mean.

FIG. 10*d* is a graphical representation showing the percentage of apoptotic AML/GMRα$^+$ cells as estimated from propidium iodide staining of DNA, following titration of cells with different concentrations of either wild-type GM-CSF protein (●), or Gm-CSF E21R protein (▬). Error bars show the standard error of the mean.

FIG. 10*e* is a graphical representation showing the percentage of apoptotic AML/GMRα$^+$ cells, as estimated from propidium iodide staining of DNA, following incubation of cells for up to 48 hours, with either wild-type G-CSF protein and GM-CSF E21R protein (○); IL-3 protein and GM-CSF E21R protein (●); or the monoclonal antibody 4D4 which neutralizes GM-CSF (Δ). Significant increases in numbers of apoptotic cells occurred following incubation of cells with Gm-CSF E21R protein and G-CSF, for 24 to 48 hours. No increase in apoptotis was observed following incubation of cells with Gm-CSF protein in the presence of IL-3, or by neutralization of GM-CSF activity using the monoclonal antibody 4D4. Error bars show the standard error of the mean.

FIG. 11 are graphic representations showing that E21R induces apoptosis of CD34$^+$/GMRα$^+$ haemopoietic progenitors.

FIG. 11*a* is a graphical representation showing the percentage of apoptotic bone marrow cells expressing CD34, CD38, and the GM-CSF-specific α-chain of the GM-CSF receptor (i.e. CD34$^+$ CD38$^+$/GMRα$^+$ cells), as estimated from propidium iodide staining of DNA, following incubation of cells, for up to 48 hours, with either G-CSF and GM-CSF E21R protein (□); wild-type Gm-CSF protein alone (●); or IL-3 and GM-CSF E21R protein (■). Significant increases in numbers of apoptotic cells occurred following incubation of cells with GM-CSF E21R protein for 24 to 48 hours, however the apoptotic effect of E21R was prevented by I1-3. Error bars show the standard error of the mean.

FIG. 11*b* is a graphical representation showing the percentage of apoptotic bone marrow cells expressing CD34, but not expressing CD38 or the GM-CSF-specific α-chain of the GM-CSF receptor (i.e., CD34$^+$ CD38$^-$/GMRα$^-$ cells), as estimated from propidium iodide staining of DNA, following incubation of cells for up to 48 hours with either G-CSF alone (■); G-CSF and GM-CSF E21R protein (□); G-CSF and IL-3 proteins (●); or G-CSF and IL-3 proteins and GM-CSF E21R protein (○). Error bars show the standard error of the mean.

FIG. 11*c* is a graphical representation showing the percentage of apoptotic bone marrow cells either lacking the GM-CSF-specific α-chain of the GM-CSF receptor [i.e. cells designated as CD34$^+$ CD38$^-$/GMRα$^-$ (column 1 in each grouping; open bars)]; or alternatively, which express the GM-CSF-specific α-chain of the GM-CSF receptor [i.e. cells designated as either CD34$^+$ CD38$^+$/GMRα$^+$ (column 2 in each grouping; back-hatched bars); or CD34$^+$/GMRα$^+$ (column 4 in each grouping; forward-hatched bars)] as estimated from propidium iodide staining of DNA, following incubation of with the following cytokine activities from top to bottom of the figure: G-CSF protein alone (G-CSF); G-CSF and GM-CSF E21R protein (G-CSF +E21R); G-CSF and wild-type GM-CSF protein (G-CSF+GM-CSF); G-CSF+E21R protein (G-CSF+IL-3););); G-CSF and IL-3 protein and GM-CSF E21R protein (G-CSF+IL-3+E21R); G-CSF and stem cell factor (G-CSF+SCF); G-CSF and stem cell factor and GM-CSF E21R protein (G-CSF+SCF+E21R); G-CSF and stem cell factor and IL-3 protein (G-CSF+SCF+IL-3); and G-CSF and stem cell factor IL-3 protein and GM-CSF E21R protein (G-CSF+SCF+IL-3+E21R). Error bars show the standard error of the mean.

FIG. 11*d* is a graphical representation showing the number of colonies formed from 500 bone marrow cells either lacking the GM-CSF-specific α-chain of the GM-CSF receptor [i.e. cells designated as CD34$^+$ CD38$^-$/GMRα$^-$ (column 1 in each grouping; open bars)]; or alternatively, which express the GM-CSF-specific α-chain of the GM-CSF receptor [i.e., cells designated as either CD34$^+$ CD38$^+$/GMRα$^+$ (column 2 in each grouping; back-hatched bars); or CD34$^+$ CD33$^+$/GMRα$^+$ (column 3 in each grouping; vertically-hatched bars); or CD34$^+$/GMRα$^+$ (column 4 in each grouping; forward-hatched bars)] following their incubation of with the following cytokine activities from top to bottom of the figure; G-CSF protein alone (G-CSF); G-CSF and GM-CSF E21R protein (G-CSF+E21R); G-CSF and wild-type GM-CSF protein (G-CSF+GM-CSF); G-CSF and wild-type GM-CSF protein and GM-CSF E21R protein (G-CSF+GM-CSF+E21R); G-CSF and IL-3 protein (G-CSF+IL-3); G-CSF and 11-3 protein and GM-CSF E21R protein (G-CSF+IL-3+E21R); G-CSF and stem cell factor (G-CSF+SCF); G-CSF and stem cell factor and GM-CSF E21R protein (G-CSF+SCF+E21R); G-CSF and stem cell factor IL-3 protein (G-CSF+SCF+IL-3); and G-CSF and stem cell factor and IL-3 protein and GM-CSF E21R protein (G-CSF+SCF+IL-3 +E21R). Error bars show the standard error of the mean.

FIG. 12 is a graphical representation showing that E21R-induced apoptosis requires transcription, protein synthesis and kinase activity. (a) Titration of genisteiii and staurosporine in the absence (open symbols) and presence (solid symbols) of E21R (1 μg/ml). (b) Titration of actinomycin D and cycloheximide in the absence (open symbols) and presence (solid symbols) of E21R (1 μg/ml). Apoptosis was measured at the 48 hr time point. Data are means and SEM of triplicate samples from one AML case and are representative of four other cases.

Figure 12B:
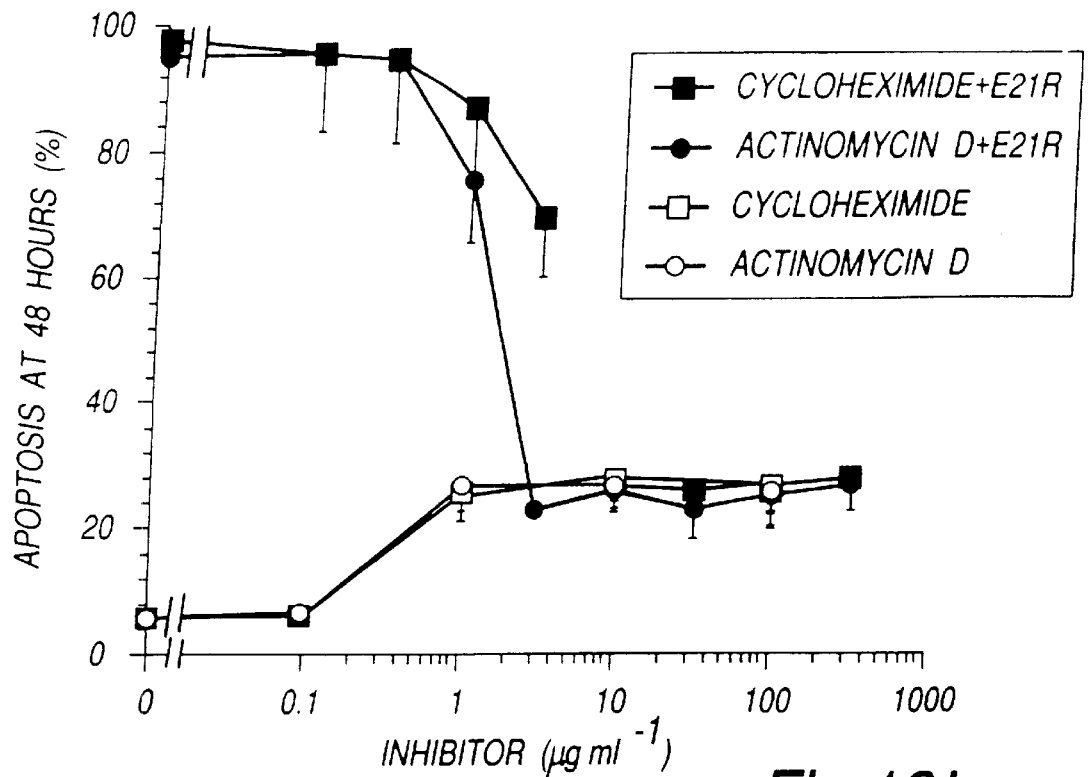
Figure 12A:
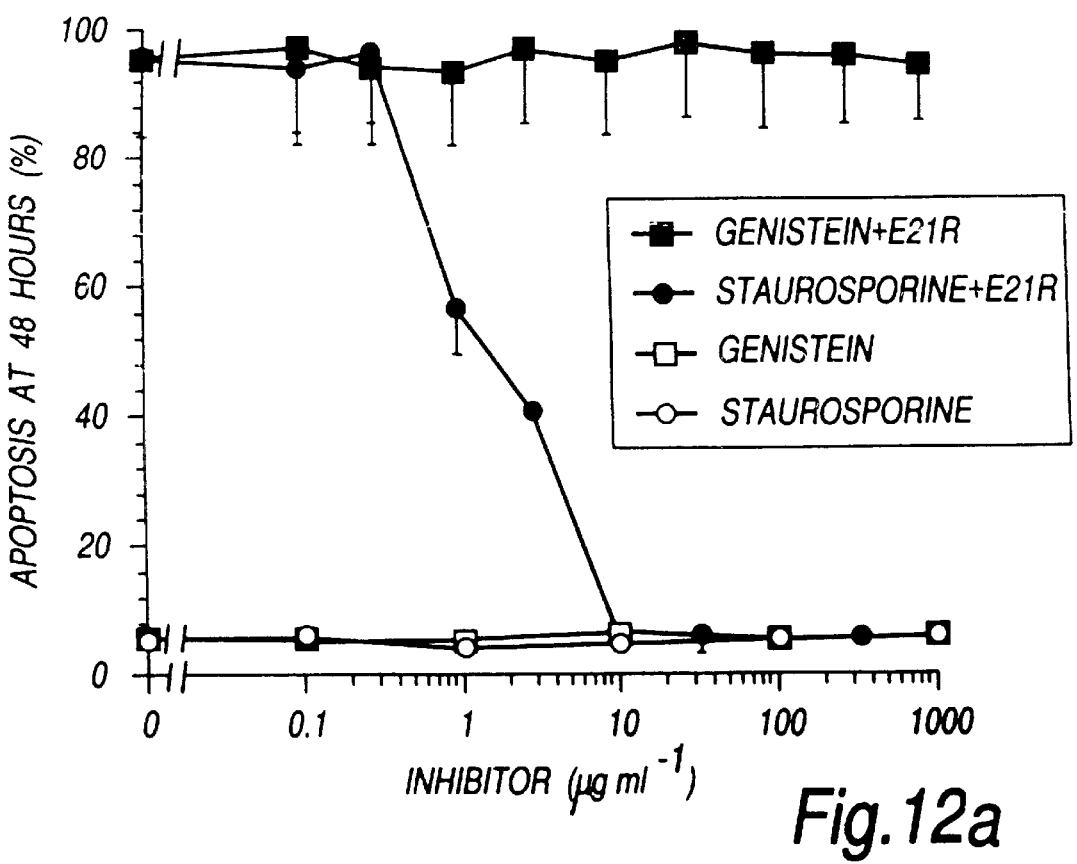

FIG. 12a is graphical representation showing the percentage of apoptotic AML cells after 48 hours incubation in the presence of different concentrations of the tyrosine kinase inhibitor genistein (□ and ●); or the protein kinase C inhibitor staurosporine (□ and ●), in the absence of GM-CSF E21R protein (□ and ○), or in the presence of GM-CSF E21R protein (∪ and ●). Inhibitor concentrations are indicated on the abscissa. The percentage of apoptotic cells in indicate on the ordinate. Error bars indicate the standard error of the mean.

FIG. 12b is a graphical representation showing the percentage of apoptotic AML cells after 48 hours incubation in the presence of different concentrations of the protein synthesis inhibitor cycloheximide (□ and ■); or the transcription inhibitor actinomycin D (○ and ●), in the absence of GM-CSF E21R protein (□ and ○), or in the presence of GM-CSF E21R protein (■ and ●). Inhibitor concentrations are indicated on the abscissa. The percentage of apoptotic cells in indicated on the ordinate. Error bars indicate the standard error of the mean.

Figure 13:
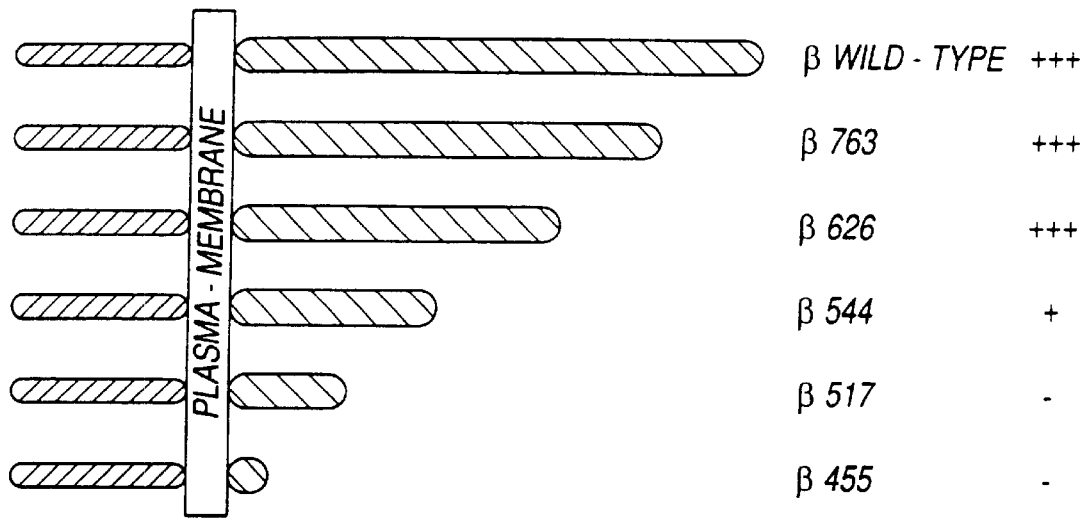
Figure 13:

FIG. 13 shows that the membrane proximal domains of both receptor chains are required for induction of apoptosis, while deletions of the more distal part of either chain did not affect E21R-mediated apoptosis.

EXAMPLE 1

CONSTRUCTION OF pBRE132 AND pBRE133 FOR EXPRESSION OF RECOMBINANT E21R PROTEIN

Construction of pBRE132 Expression Plasmid

A synthetic DNA cassette was constructed by annealing two oligonucleotides, TATGTTCGCTACT7CAAGCTCTACGGGGAACGATAT CGCTGGCAGCCA (SEQ ID NO: 1) and AGCfTGGCTG-CAGCGATATCGTTCCCCGTAGAGCT-TGAAGTAGCGAACA (SEQ ID NO:2) at 65° C. for 5 min in 200 mM NaCl. The synthetic DNA cassette was cleaved with NdeI/HindIII and cloned into pEC611 expression vector (A. Brumby, 1987 "A vector for high expression of native proteins", Honours Thesis, University of Adelaide), generating pBRE132 (FIG. 1).

Construction of pBRE133 (E21R Expression Vector)

Figure 2:
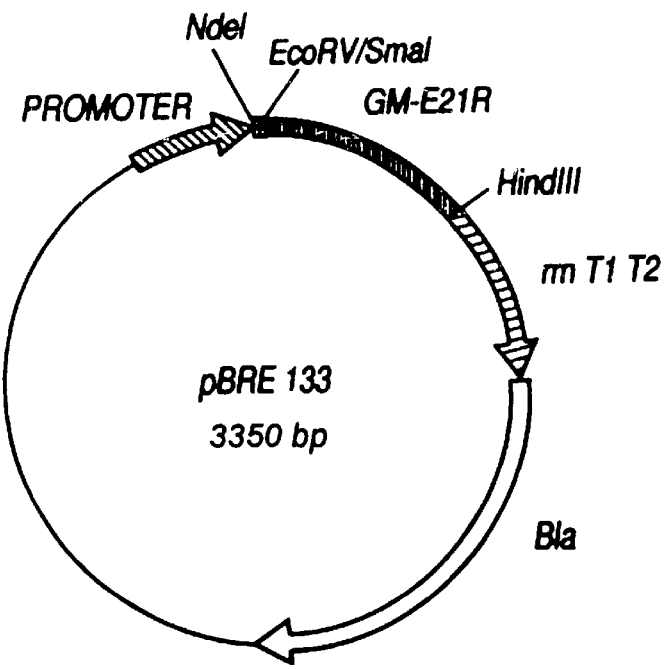
Figure 3:
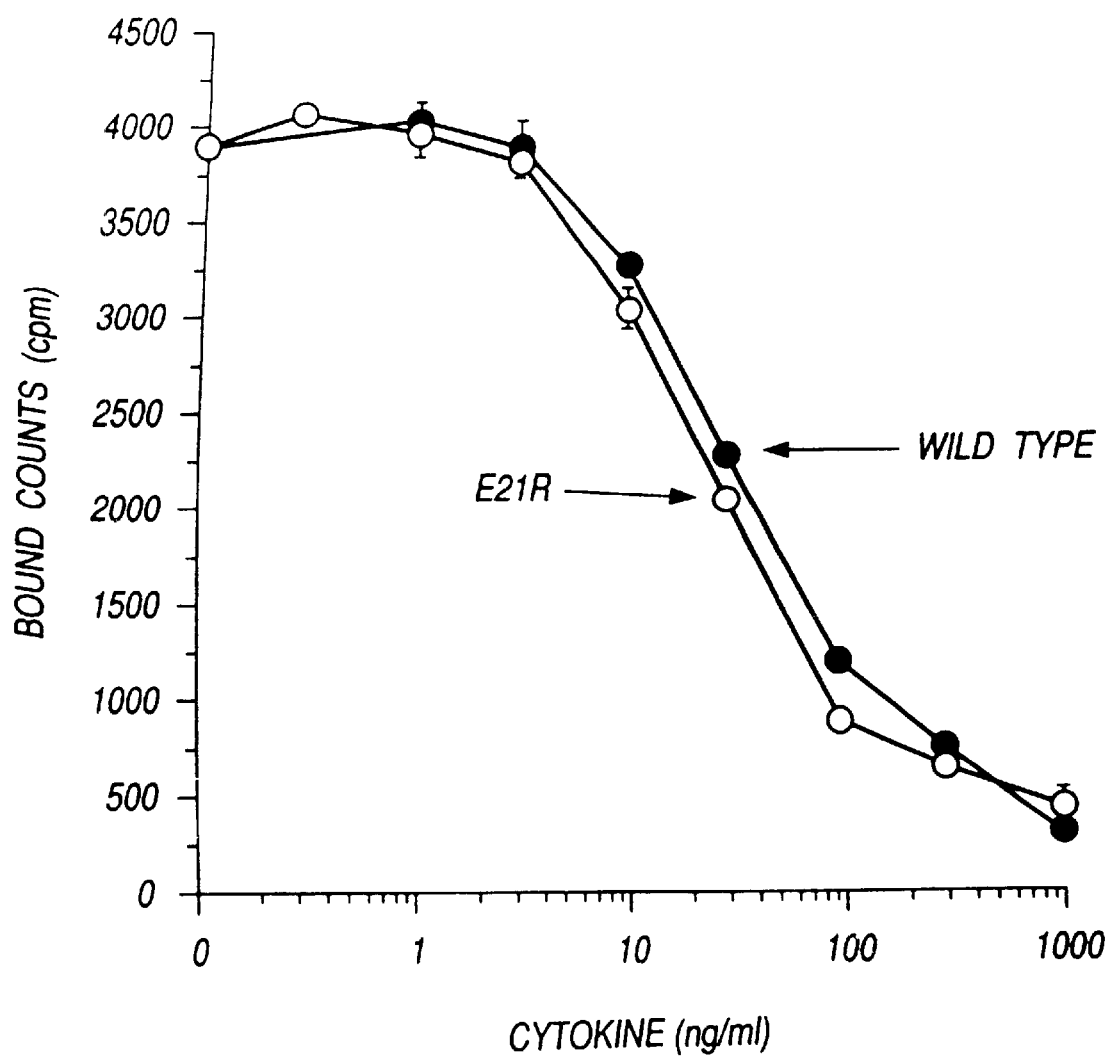
Figure 4:
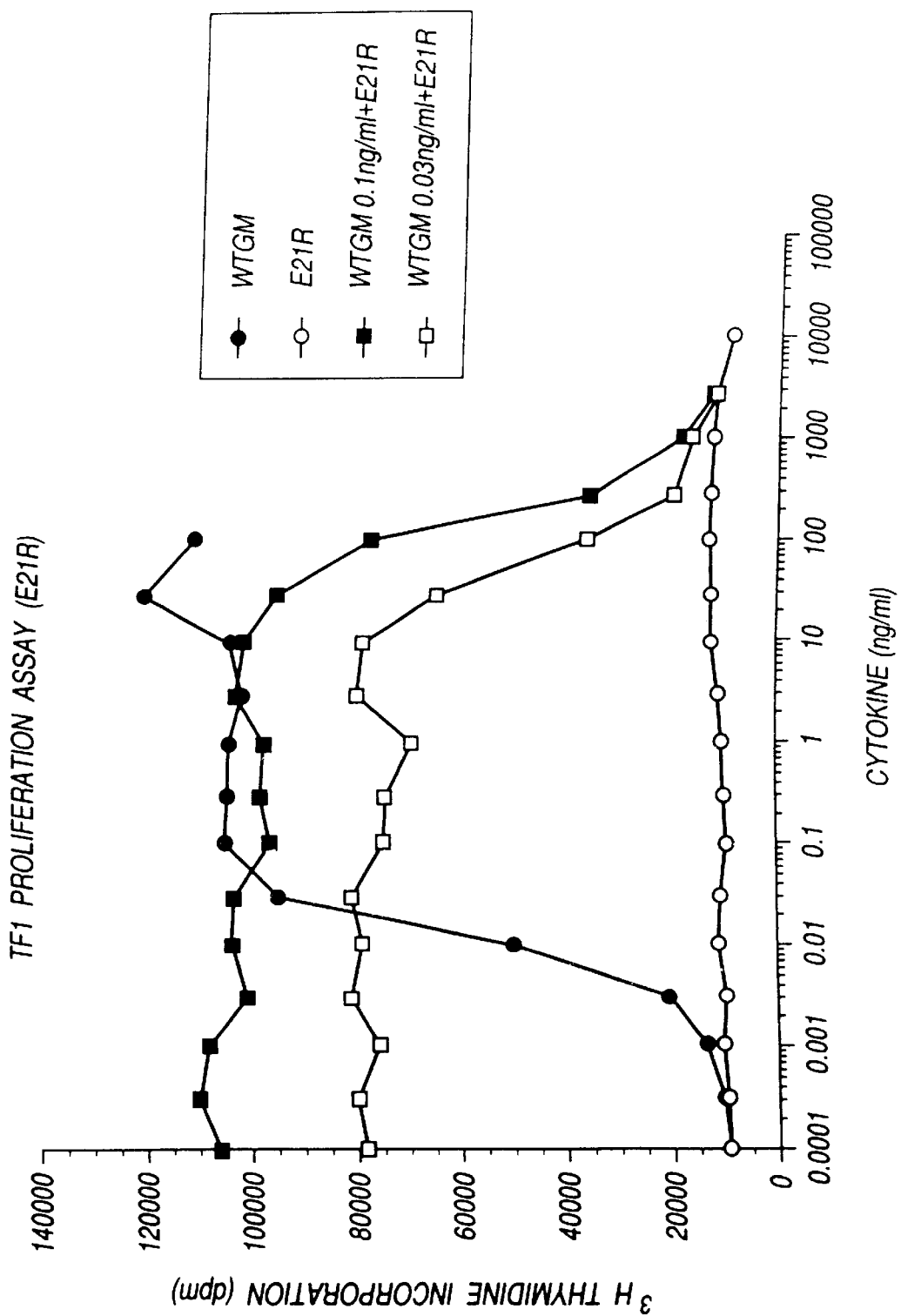
Figure 5:
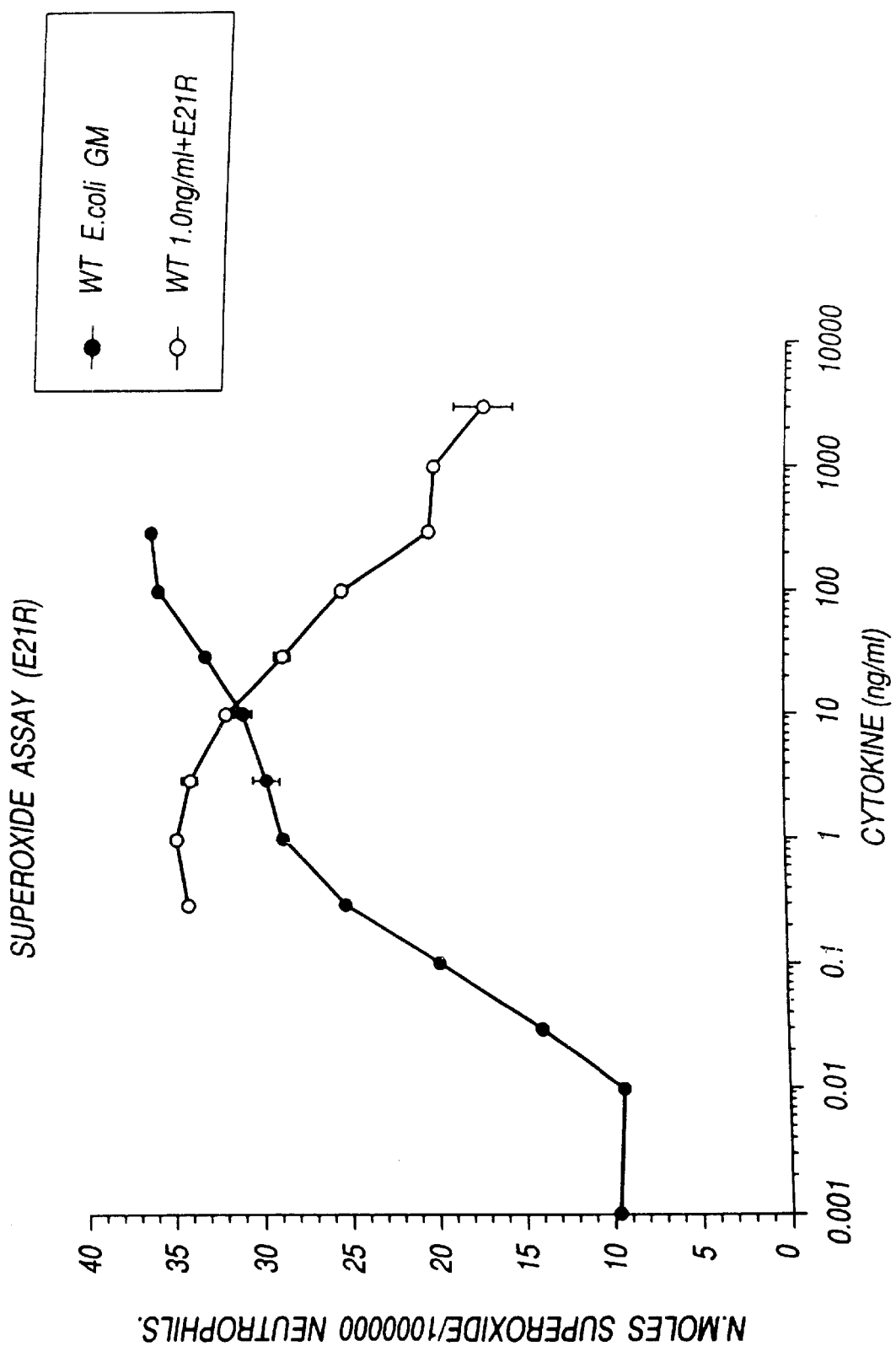
Figure 6:
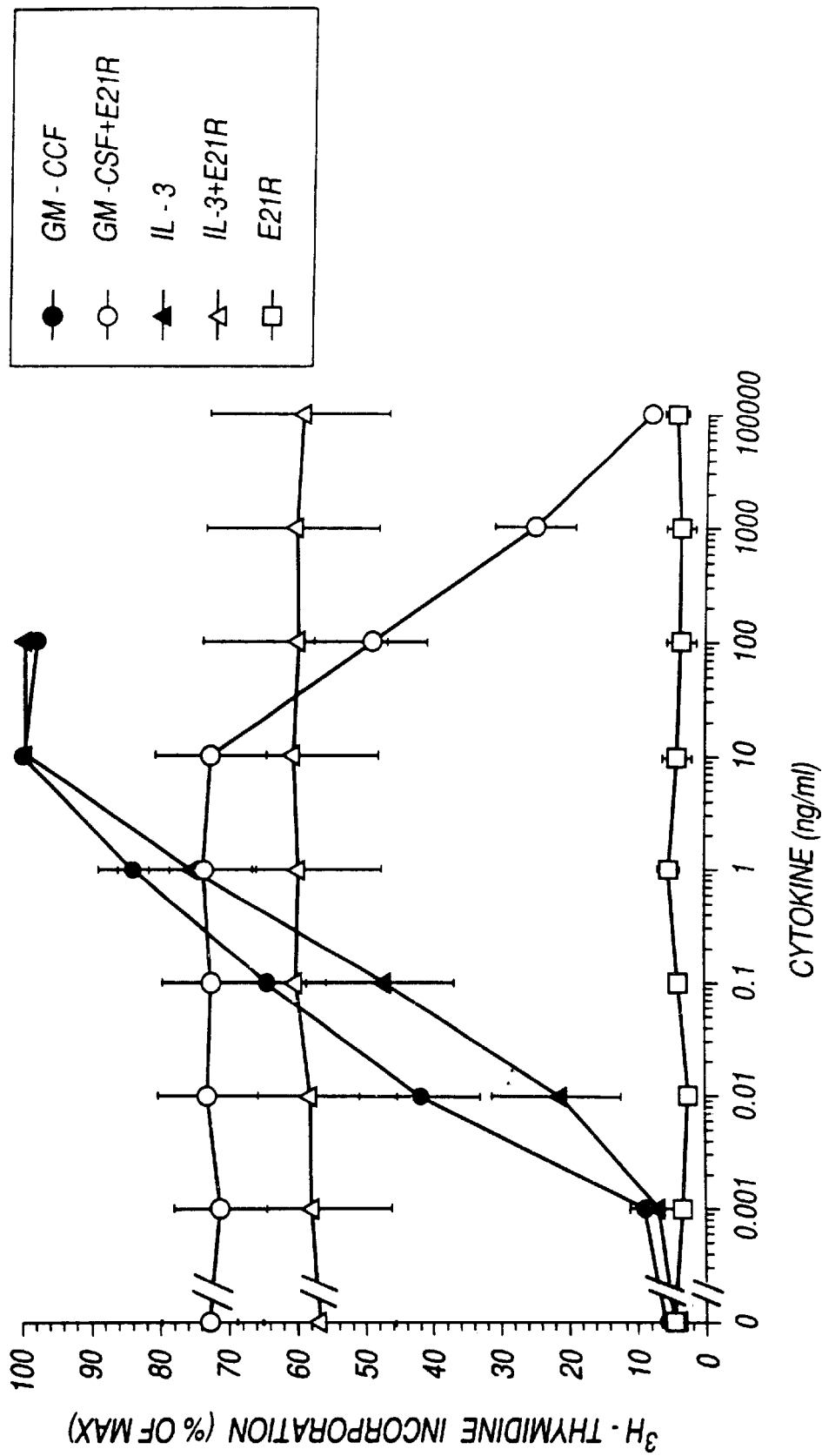
Figure 7:
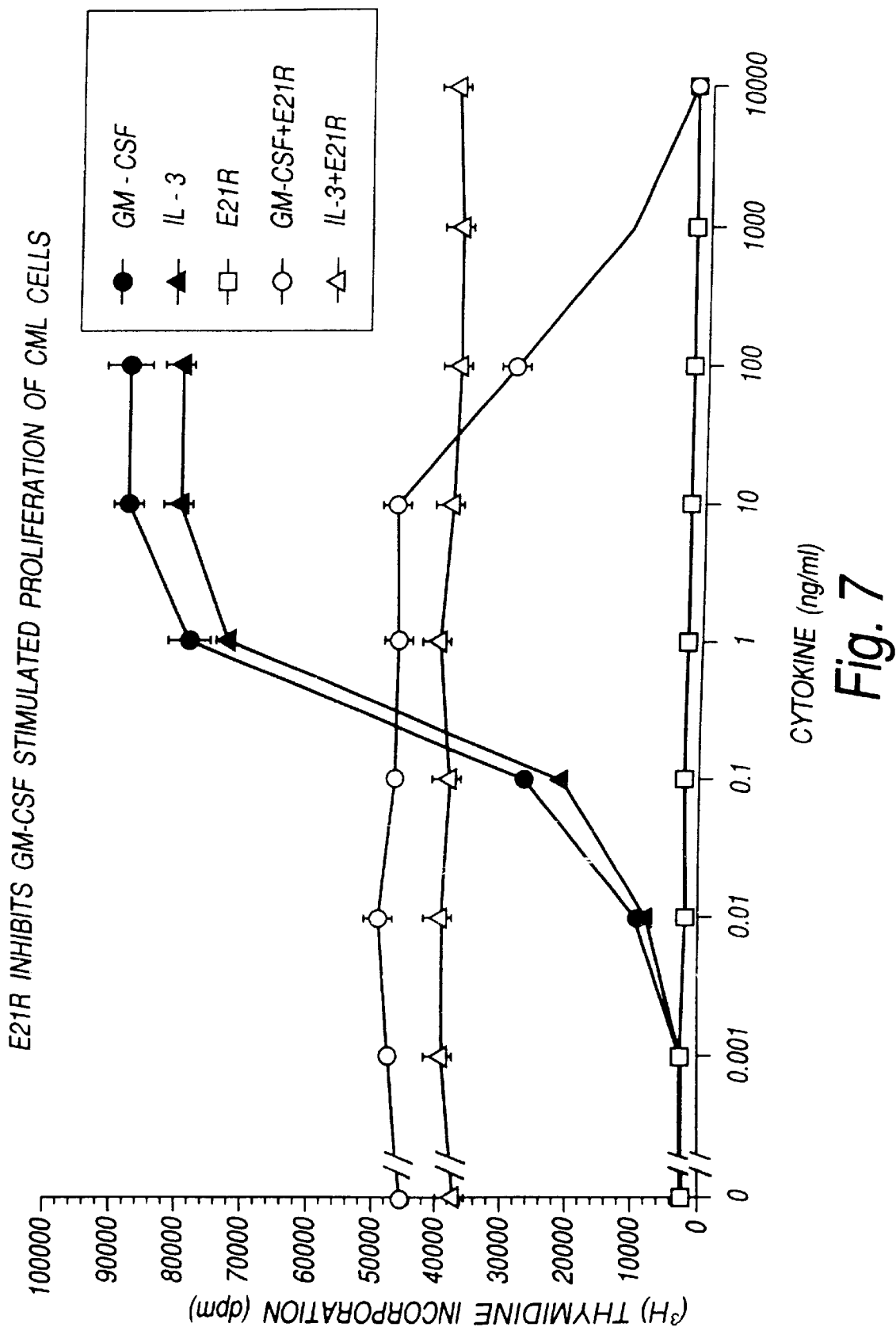
Figure 8:
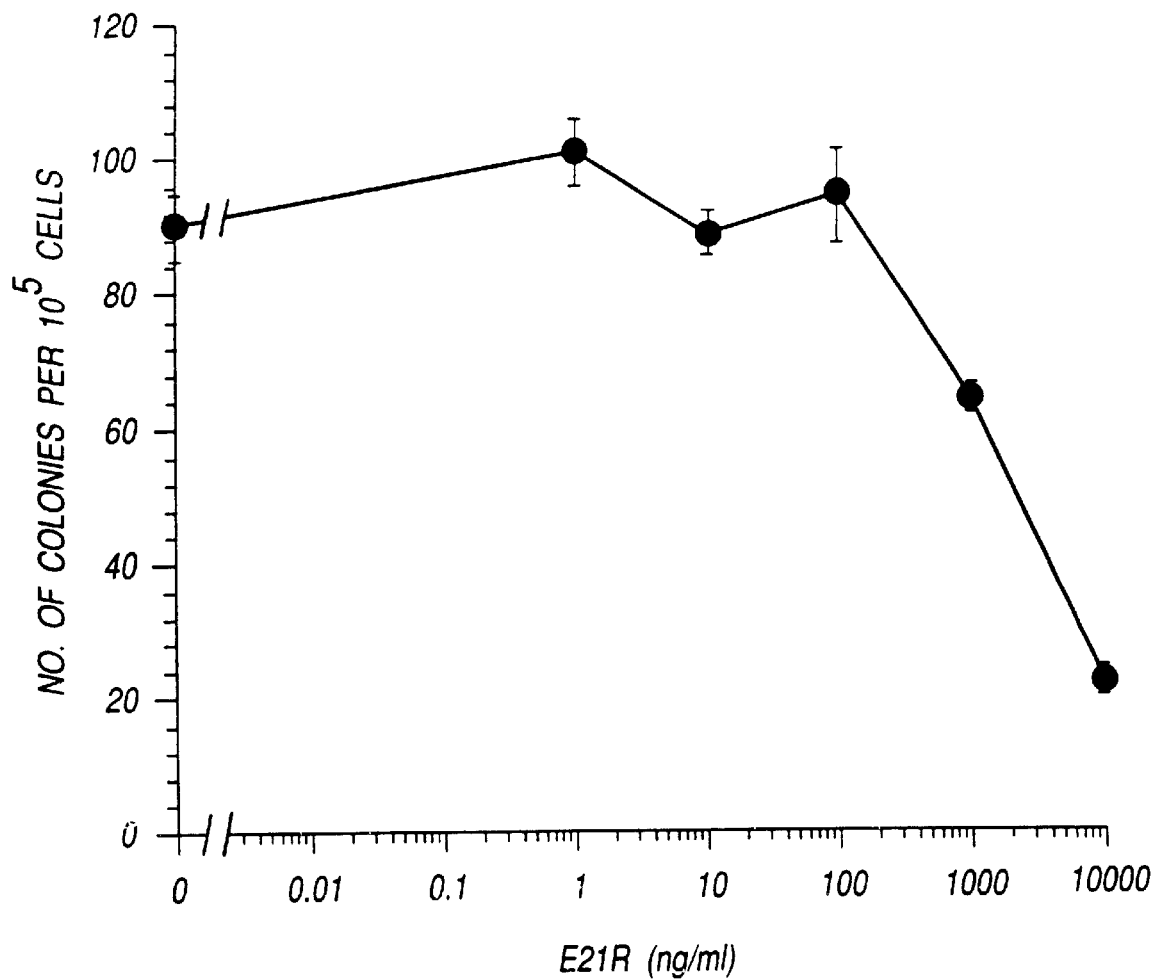

GM-CSF (E21R) cDNA was amplified employing PCR primers with unique SmaI and HindIII sites. The PCR products were cleaved with SmaI/HindIII and cloned into the EcoRV/HindIII sites of pBRE132 generating pBRE133 (FIG. 2).

Expression of pBRE133 in *Eschetichia coli* MM294/pACYCiac Expression analysis demonstrated that pBRE133 in *Escherichia coli* MM294/pACYCiac expressed inclusion bodies (IB) consisting of recombinant E21R protein, as judged by microscopy examination, standard SDS-PAGE and mass spectometry analysis of the purified protein.

EXAMPLE 2

Production of Granulocyte Macropage Colony Stimulating Factor Antagonists E21R 1. Fermentation
A. Inoculation 1. *Escherichia coli* MM294/pACYClac carrying pBRE133 was streaked out from a 80° C. glycerol stock onto a minimal medium plate containing ampicillin (100 μg/ml) and kanamycin (30 μg/ml) and grown overnight at 37° C.

2. Multiple colonies were assessed for GM-CSF (E21R) expression levels by microscopic examination of 20 ml shake flask cultures containing inducer, or by colony size on agar plates with or without inducer, in this instance with IPTG.

3. The selected single colony from an agar plate was transferred into 20 ml of nitrogen-rich minimal medium (2) containing amplicillin (100 μg/ml)+kanamycin (30 μg/ml). The culture was grown at 37° C. overnight with agitation.

4. An amount of 10 L of C2 was sterilised in a 22 L fermenter and inoculated to a very low density with overnight culture. Growth was at 37° C. and a pH of 7.0 was maintained by the addition of 12.5 M $NH_4OH$.

5. Agitation was manually controlled and aeration automatically controlled with oxygen saturation levels remaining above 10% $pO_2$. Following depletion of glucose at 16–18 hours the cell mass was fed with a concentrated glucose solution containing additional salts. Nutrient feed flow rate was determined by pH or oxygen saturated levels.

B. Induction

1. At an optical density of $A_{600}$=50–60 the recombinant expression of E21R antagonist was induced, in this instance by the addition of IPTG. The culture was supplemented with amino acids at the time of induction (T=0) and at T=2 hours. Induction continued for 4 hours at 37° C., pH 7.0. Samples were removed at T=0,1,2,3 & 4 hours and examined by microscopy for the presence of IB, their size being determined by disc centrifugation.

2. The culture was stored overnight at 4° C.

2. PRIMARY ISOLATION OF GM-CSF (E21R) INCLUSION BODIES

1. Homogenization

Step 1

The culture was passed five times through a Gaulin 30CD homogenizer at 13500 psi, with homogenate being cooled between passes. Homogenate was then diluted with an equal volume of RO $H_2O$.

The IB size was redetermined by disc centrifugation.

2. Centrifugation

Step 1

The homogenate was centrifuged in a Westfalia SB-7 separator with a constant speed of 9210 rpm at a flow rate determined by IB size.

The concentrate collected from this first step was diluted to ≦2.5% v/v.

3. Homogenization

Step 2

The IB suspension was passed once through a Gaulin 30CD homogenizer at 13500 psi.

The IB size was again determined by disc centrifugation.

4. Centrifugation

Step 2

The homogenate was centrifuged in a Westfalia SA-1 separator with a constant speed of 9700 rpm at a flow rate determined by IB size.

EXAMPLE 3

GM-CSF Antagonist (E21R) Purification

The inclusion body (IB) solution is first washed with an equal volume of a mild buffered denaturant such as 2M guanidine hydrochloride (GuHCl). The solution is stirred gently at 4° C. for 30 minutes. The washed IB can then be recovered with a low speed centrifuge spin. The washed IB are then resuspended in a small volume of water (e.g. Milli Q), immediately prior to dissolution and refolding.

Dissolution, refolding and oxidation of the GM-CSF antagonist (E21R) IB is initiated by dissolving the washed IB in an unbuffered urea solution at an alkaline pH. To ensure complete dissolution of the IB, the concentration of urea should be between 2.5M and 4M and the pH between 11 and 12. The concentration of protein can be between 0.5 and 5 mg/ml. These three parameters can be varied depending on the purity of the IB preparation. The stirred solution is maintained at an alkaline pH with a sodium hydroxide solution (e.g. 2M NaOH), until it can be seen that refolding and oxidation has reached equilibrium. The extent of refolding to the correct fold for GM-CSF can be monitored by chromatographic means, e.g. reversed phase HPLC (RP-HPLC) or size-exclusion chromatography (SEC), comparing the chromatographic profile to that of a known folded standard of GM-CSF. Once refolding has reached equilibrium, the pH of the solution is lowered to a less alkaline pH, (e.g. pH 9.1) with a concentrated solution of a suitable buffer (e.g. 0.5M sodium boratc pH 9.1).

The correctly refolded GM-CSF antagonist (E21R) can then be purified from incorrectly folded and aggregated forms using chromatography, e.g. anion-exchange chromatography (IEC) or RP-HPLC. For example, the refolding solution from above is loaded onto a anion-exchange column (e.g. Q-Sepharose Fast flow [Pharmacia]). Upon completion of loading, the column is washed with two column volumes of a low salt buffer. The correctly folded form of GM-CSF antagonist (E21R) is eluted from the column with a gradient of sodium chloride (e.g. 0–500 mM NaCl over ten column volumes). The column eluent can be analysed for GM-CSF antagonist (E21R) purity by either SEC (e.g. Superose 12 [Pharmacia]), or RP-HPLC (e.g. Brownlee butyl-silica column (100 mm×2.1 mm i.d.) employing 0.1% v/v TFA in water as Buffer A and 0.1% v/v TFA in acetonitrile as Buffer B).

The purified GM-CSF antagonist (E21R) can then be desalted (e.g. Sephadex G-25) into a suitable buffer (e.g. 5 mM $Na_2HPO_4$ pH 7.6) in preparation for formulation and lyophilisation. The desalted protein can be quantitated by its absorption at 280 nm in a spectrophotometer using a $_{280}A^{1\%}$ of 9.09. Following quantitation, 1 part glycine and 5 parts mannitol, by weight, are added to the desalted protein solution. The solution is stirred gently until all solids are dissolved. If necessary, the pH is adjusted to pH 7.6 with 1M NaOH or 25% w/v orthophosphoric acid. The solution is then sterilised by filtration (0.2 μm), aliquoted into sterile glassware and lyophilised.

EXAMPLE 4

E21R Exhibits Antagonistic Properties

Purified E21R bound the GM-CSF receptor α-chain with the equivalent potency as wild type GM-CSF (FIG. 3). In addition, E21R did not directly stimulate TF-1 cell proliferation (FIG. 4) or neutrophil $0_2$-release but instead antagonised the stimulatory effect of GM-CSF in both functional assays (FIGS. 4 and 5). Using cells from patients with acute myeloid leukaemia (AML) the inventors found that E21R antagonised the stimulation of AML, cell proliferation; by GM-CSF in a dose-dependeiit manner (FIG. 6). This was specific for GM-CSF in that E21R did not antagonise IL-3-mediated proliferation (FIG. 6). E21R completely antagonised the proliferative effect of GM-CSF on cells from patients with chronic myeloid leukaemia (CML) (FIG. 7).

EXAMPLE 5

E21R Inhibits Colony Formation by Juvenile Chronic Myloid Leukemia (JCML) Cells JCML is a rare disease which is generally diagnosed in children under 2 years. There is no effective therapy for this condition and it is invariably fatal 2–3 years after diagnosis. Cells from JCML patients grow spontaneously in culture probably due to autocrine production of GM-CSF feeding back on these cells.

It was found that E21R inhibited the growth of JCML in a dose-dependent manner (FIG. 8). This may be due to blocking autocrine GM-CSF, induction of apoptosis (see below), or a different mechanism.

EXAMPLE 6

Since E21R binding to the α-chain antagonized GM-CSF stimulated cell function, the inventors reasoned that E21R might interfere with cell survival. The life span of malignant cells expressing the GM-CSF receptor from patients with either acute (AML) or chronic (CML) myeloid leukaemia was studied. When these cells were incubated with E21R, chromosomal DNA was degraded into low-molecular weight fragments, a salient feature of apoptosis (FIG. 9).

E21R caused DNA from myeloid leukaemic cells to degrade. DNA degradation was absent in cells incubated with either GM-CSF alone or medium only. The data are from one AML case and representative of 20 other cases. Normal bone marrow (BM) cells expressing CD34/GMRα, $CD34^+/CD38\_/GMR\alpha^-$ and CD34/CD33/GMRα also underwent apoptosis with E21R. In the $CD34^+/CD38^-/GMR\alpha^-$ or population, DNA degradation was not present. The data are from one BM case and representative of two other cases. Markers of known molecular sizes in kilobases (kb) are shown. Peripheral blood cells from patients with AML (all FAB subtypes) at diagnosis were Ficoll separated. The T lymphocytes were removed by incubation with a mouse anti-human CD3 monoclonal antibody followed by a rabbit anti-mouse antibody coupled to a magnetic bead (Miltenyi Biotech, Gladbach, Germany). The AML population consisted of >99% blasts. Bone marrow progenitors were collected from a healthy donor and the $CD34^+$ subsets were sorted by flow cytometry (FACStarPLUS, Becton-Dickinson, N.J.). Cells that expressed the GMRα were isolated using an anti-GMRα monoclonal antibody and a magnetic bead procedure. The cells were incubated in RPMI 1640 medium with 10% v/v fetal calf serum (FCS), antibiotics, sodium bicarbonate, and L-glutamine for 48 h at 37° C. To the cultures either *E. coli*-derived E21R (1 μg/ml) or GM-CSF (0.3 ng/ml, Genetics Institute, Cambridge, Mass.) were added. The medium used to culture bone marrow cells contained G-CSF (10 ng/ml, Amgen, Thousand Oaks, Calif.). DNA was extracted and analyzed after agarose gel electrophoresis.

Incubation of the cells with either GM-CSF alone or medium only for up to 48 h caused no degradation of the DNA. Staining of DNA with propidium iodide from one AML case revealed that a 48-h incubation with E21R (1 μg/ml) caused apoptosis of almost all the cells FIG. 10(*a*). The G0/G1, S and G2/M regions represent cells in various phases of the cell cycle, while the subdiploid Ap peak denotes apoptotic cells. To quantify the number of apoptotic cells, the DNA binding of propidium iodide was measured. Initially about 75% of AML cells underwent apoptosis in the presence of E21R at 48 h. This proportion of apoptotic cells correlated well with the number of cells expressing the GM-CSF α receptor. E21R (1 μg/ml) induced apoptosis in 21/21 AML cases (FIG. 10b) and 14/14 CML cases (FIG. 10c).

Figure 10A:
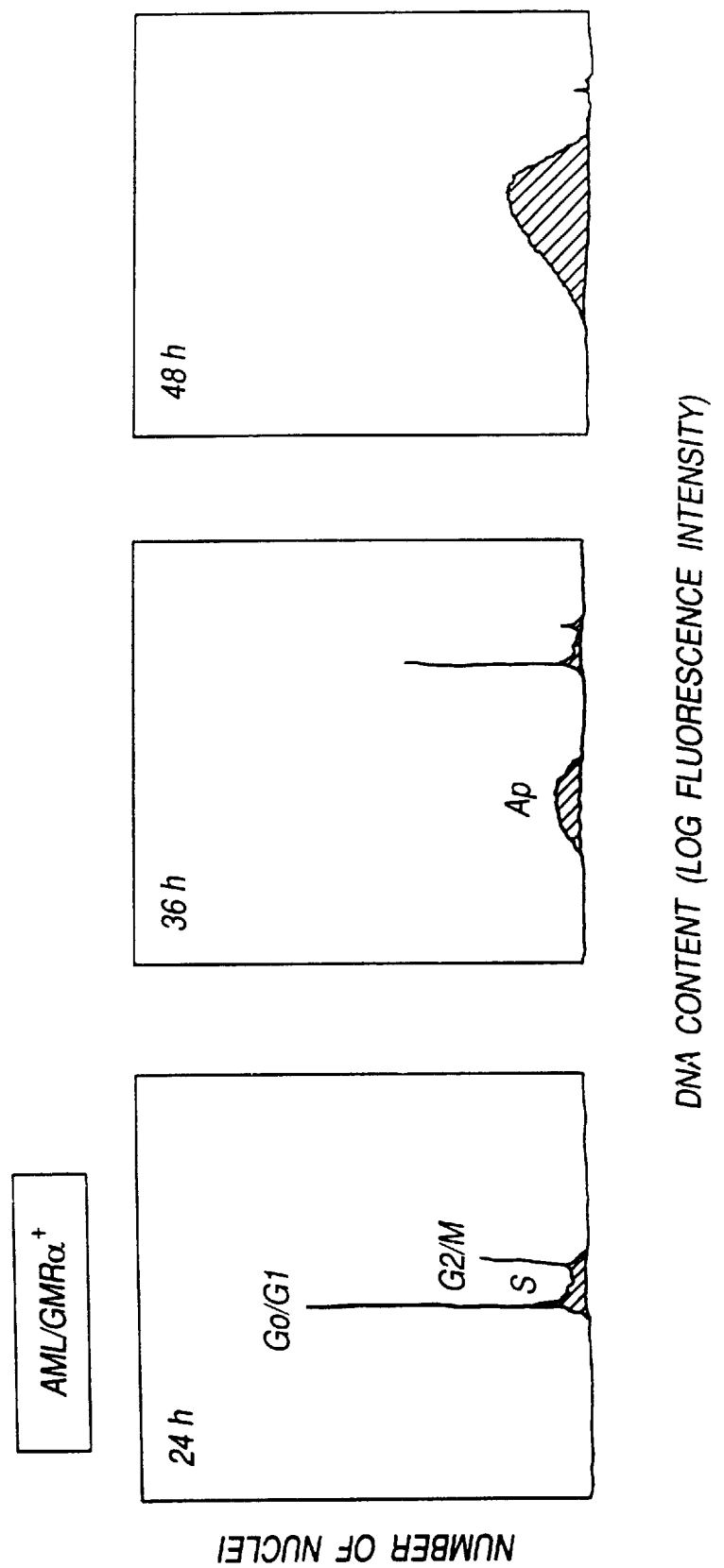
Figure 10B:
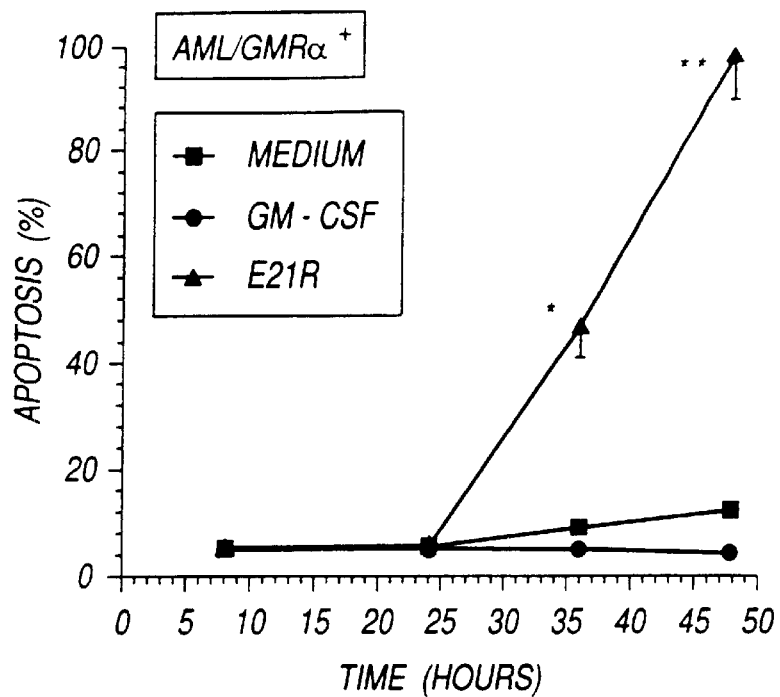
Figure 10C:
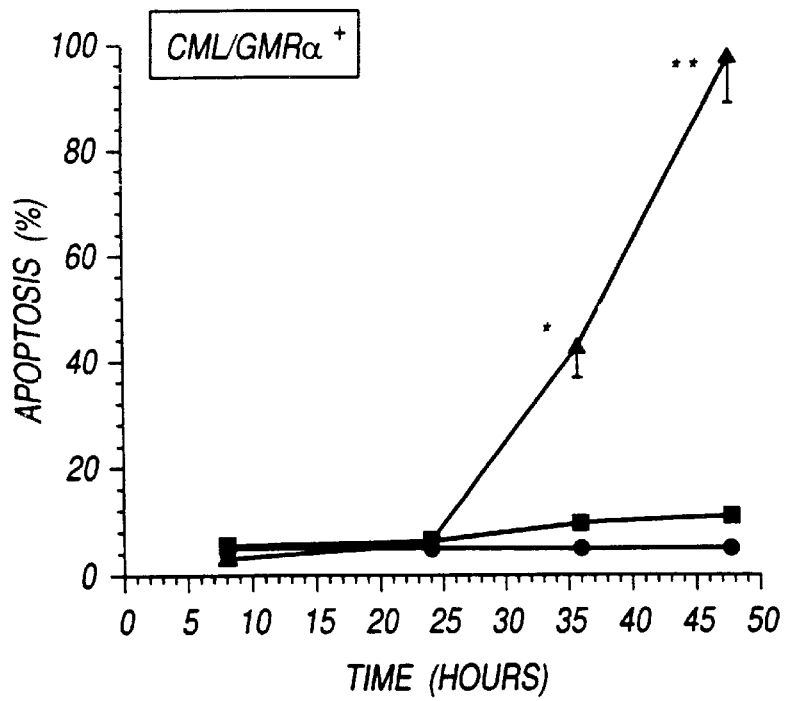

To examine whether the apoptotic effect of E21R was secondary to antagonism of GM-CSF present in the culture conditions or due to a direct effect to E21R, several controls were performed. First, it is known that while normal bone marrow haemopoietic cells do not express the GM-CSF mRNA, some AML cells can produce GM-CSF. However, GM-CSF was detected in supernatants of only 8 out of 21 AML cases. The other 13 cases did not show detectable GM-CSF in the supernatants, and an RNase protection assay showed lack of mRNA for GM-CSF. Second, biologically active GM-CSF in the culture medium was not present. enumeration of apoptotic cells in serum-free medium yielded similar results as depicted in FIG. 10b, and the neutralising anti-GM-CSF monoclonal antibody 4D4 did not induce apoptosis of the AML cells (FIG. 10e). Finally, to determine whether any GM-CSF was bound to the AML cells when transferred ex vivo to the in vitro cultures, the inventors measured the cell surface-associated binding of $^{125}$-labelled GM-CSF before and after acid elution. No differences were observed in specific GM-CSF binding, indicating that the cells were not carrying over receptor-bound GM-CSF. E21R did not induce apoptosis of myeloid cells lacking GMRα indicating that E21R was not toxic.

Figure 10D:
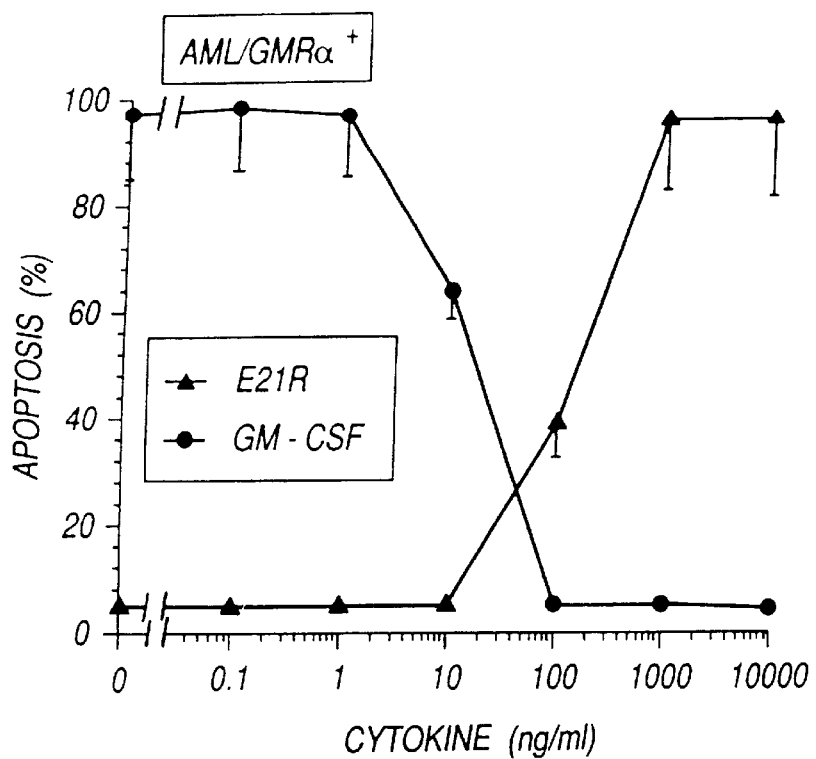
Figure 10E:
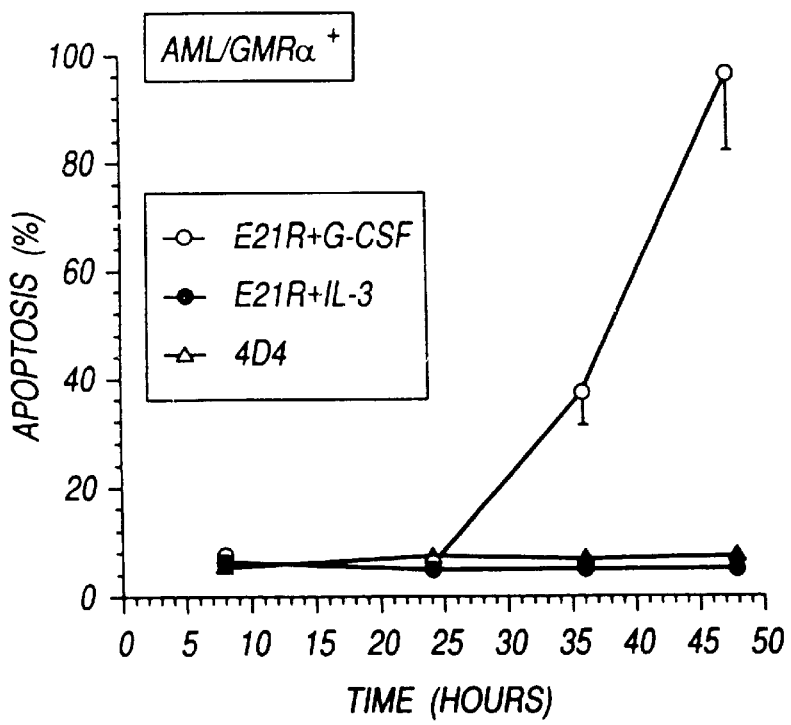

A titration of E21R showed that full apoptotic effect was achieved with 1 μg/ml FIG. 10(d). A GM-CSF concentration of 100 ng/ml effectively inhibited E21R (1 μg/ml) mediated apoptosis FIG. 10(d). Values are the mean and s.e.m. of three replicates from one AML case.

When combined with G-CSF (10 ng/ml), but not with IL-3 (10 ng/ml, Genetics Institute), E21R induced apoptosis of nearly all the cells FIG. 10(e). Peripheral blood cells were collected from untreated CML patients (all Philadelphia chromosome positive) in blast crisis and processed as for the AML cells described above. Apoptosis was determined by flow cytometry as the reduced amount of propidium iodide bound by DNA after incubating triplicate cultures of the cells overnight in a buffer containing 0.1% v/v Triton X-100 and propidium iodide (50 mg/ml).

EXAMPLE 7

Figure 9:
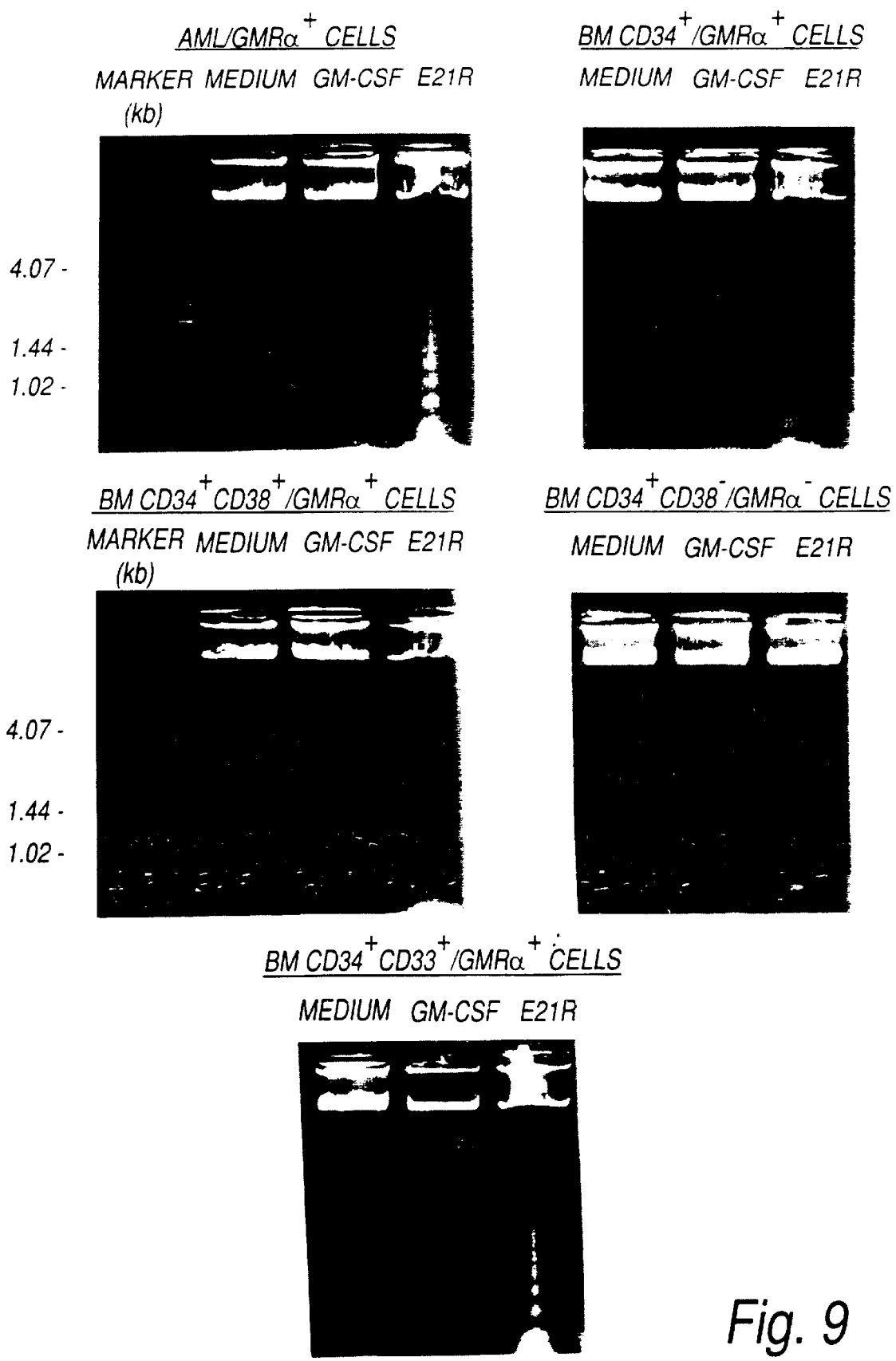

Similar to normal haemopoiesis, myeloid leukaemic cells stem from a small pool of highly proliferative progenitors that express the CD34 surface marker. To examine whether the effect of E21R was a general phenomenon related to the GMRα.expression or restricted to malignant cells, the effect of E21R on the survival of normal CD34$^+$ progenitors was studied. Bone marrow cells were fractionated by flow cytometry into total CD34$^+$, CD34$^+$CD38$^+$ (committed), and CD34$^+$CD33$^+$ (myeloid committed) progenitors and the apoptotic fractions determined after E21R treatment. DNA fragmentation was present in the CD34$^+$/GMRα$^+$, CD34$^+$CD38$^+$/GMRα$^+$, and CD34$^+$CD33$^+$/GMRα$^+$ subsets, but not amongst the non-committed CD34$^+$CD38$^-$ cells, the latter subset lacking GMRα (FIG. 9). Analysis of DNA binding of propidium iodide revealed that E21R caused apoptosis of the cells in the CD34$^+$CD38$^+$/GMRα$^+$ (FIG. 11a,c), CD34$^+$/GMRα$^+$, and the CD34$^+$CD33$^+$/GMRα$^+$ populations (FIG. 11c), but not on cells lacking the GM-CSFRα chain (FIG. 11b, c).

Figure 11A:
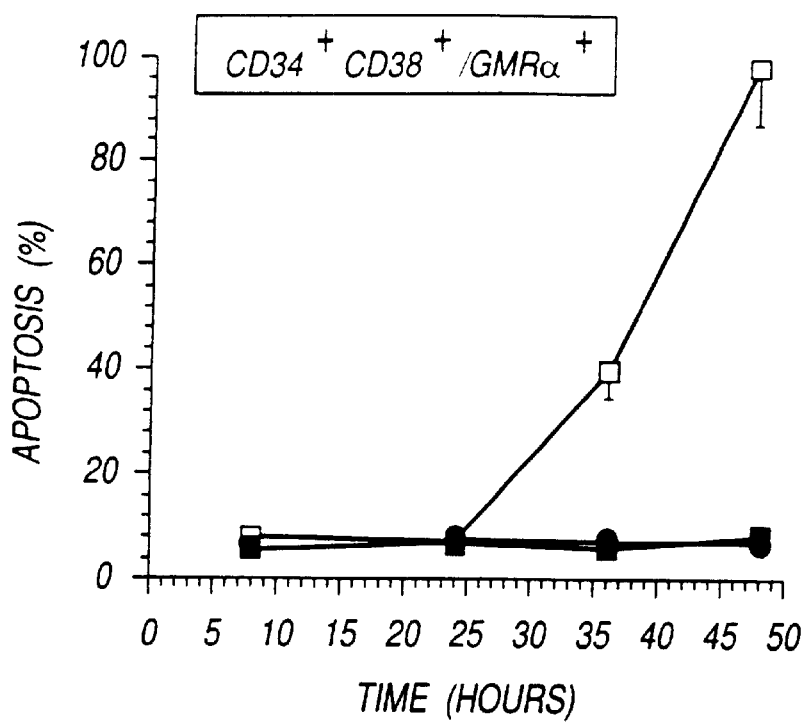
Figure 11B:
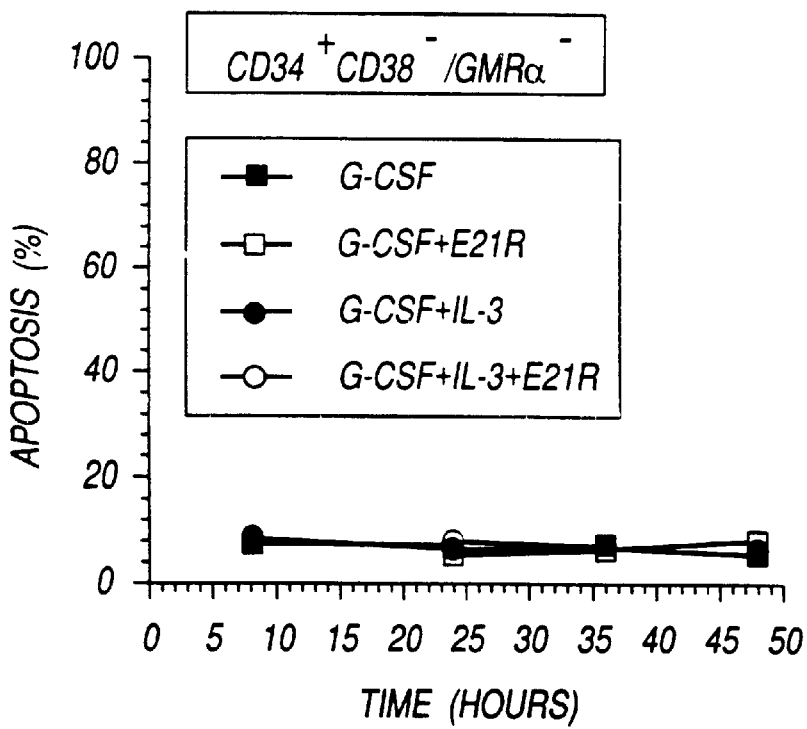

E21R in medium with G-CSF induced apoptosis of the CD34$^+$CD38$^+$/GMRα$^+$ committed progenitors FIG. 11(a), but not of the CD34$^+$CD38$^+$/GMRα$^-$ cells FIG. 11(b). When combined with G-CSF and either GM-CSF or stem cell factor (SCF), E21R caused apoptosis of all CD34$^+$/GMRα$^+$ subsets after 48 h, while the addition of IL-3 prevented apoptosis FIG. 11(a,c). The non-committed CD34$^+$CD38$^-$ GMRα$^-$ cells were not affected by E21R treatment FIG. 11(b, c). Values are the mean and s.e.m. from three cases. Studies of colony formation by CD34$^+$/GMRα$^+$ committed progenitors showed that E21R in combination with either G-CSF, or G-CSF plus GMCSF, or G-CSF plus SCF virtually abolished colony growth, while E21R plus G-CSF and IL-3, or E21R plus G-CSF, SCF and IL-3 did not inhibit colony growth of committed cells FIG. 11(d). Colony growth of the non-committed CD34$^+$CD38$^-$/GMRα$^-$ subset was not affected by E21R FIG. 11(d). Data from the three cases in FIG. 11(a), values are mean+s.e.m.

The bone marrow cells were collected and processed as described above. Apoptosis was measured as a reduced DNA binding of propidium iodide as outlined above. Colonies (>40 cells) of haemopoietic CD34$^+$ progenitors in a methylcellulose assay were prepared and scored after 14 days. To triplicate cultures the inventors added various combinations of E21R (1 μg/ml), G-CSF (10 ng/ml), GM-CSF (10 ng/ml), and SCF (10 ng/ml, Amgen).

Upon purification of GMRα positive cells with an anti-GMRα nonoclonal antibody, virtually 100% of the cells were apoptotic with E21R (FIG. 10a). The results were observed in 21/21 AML cases (FIG. 10b) and 14/14 CML cases (FIG. 10c) when E21R was given at a dose of 1 μg/ml, a concentration ensuring high GMRα occupancy. This concentration was based on a titration experiment where 1 μg/ml of E21R yielded maximal apoptosis (FIG. 10d). The effect was dependent on E21R binding to GMRα since a titration of GM-CSF against 1 μg/ml of E21R showed that at a concentration of 100 ng/ml GM-CSF totally abolished the apoptotic effect of E21R (FIG. 10d).

EXAMPLE 8

To test the finding in Example 7, the effect of E21R combined with either G-CSF, whose receptor is a homodimer distinct from the GM-CSF receptor, or IL-3, whose receptor is a heterodimer in which βc is shared with the GM-CSF receptor was examined; leukaemic cells expressing functional receptors for these cytokines were used. The leukaemic cells underwent apoptosis when they were incubated with E21R and G-CSF, but not with E21R and IL-3 (FIG. 10e), indicating that involvement of the βc chain is essential for survival. Since only 6/21 AML and 3/14 CML cases expressed the IL-3 receptor, this example shows that E21R might be beneficial in the treatment of the majority of leukaemias.

To rule out the possibility that the apoptotic effect of E21R was secondary to antagonism of GM-CSF present in the culture conditions, several controls were performed. First, it is known that some AML and CML cells can produce GM-CSF. With the use of a sensitive proliferation assay (lower detection limit 10 pg/ml), biologically active GM-CSF was not in the CD34$^+$CD38$^-$/GMRα$^-$ cells (FIG. 11b,c). Apoptosis by E21R was seen even if two other survival factors, G-CSF and stem cell factor (SCF), were present (FIG. 11a,c). However, when IL-3 was added to the medium, the haemopoietic progenitors expressing GMRA were rescued from apoptosis (FIG. 11a,c).

EXAMPLE 9

Since E21R directly induced apoptosis, the inventors examined the possible signaling requirements of this active process. A dose-response experiment showed that the specific tyrosine kinase inhibitor genistein did not affect E21R-induced apoptosis (FIG. 12a). In separate control experiments genistein (0.1–10 μg/ml) blocked GM-CSF (0.3–1 ng/ml)-mediated stimulation of tyrosine phosphorylation in AML cells. The protein kinase C inhibitor staurosporine profoundly inhibited the E21R-induced apoptosis when given at a dose of 10 μg/ml (FIG. 12a), suggesting that serine/threonine kinases may be central to the apoptotic mechanism of E21R. Furthermore, the inventors found that inhibition of transcription by actinomycin D or of protein synthesis by cycloheximide greatly reduced E21R-induced apoptosis of AML cells in a dose-dependent manner (FIG. 12b).

EXAMPLE 10

Figure 11C:
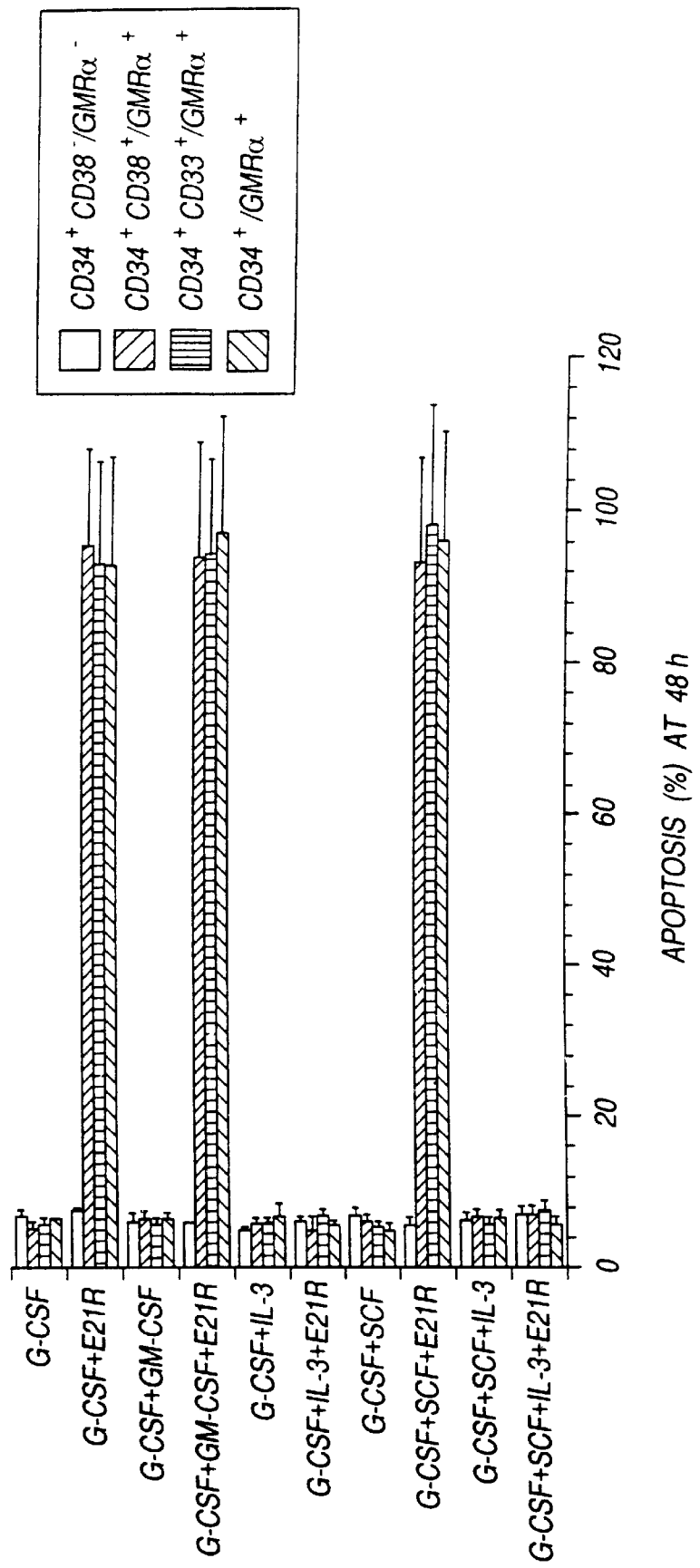
Figure 11D:
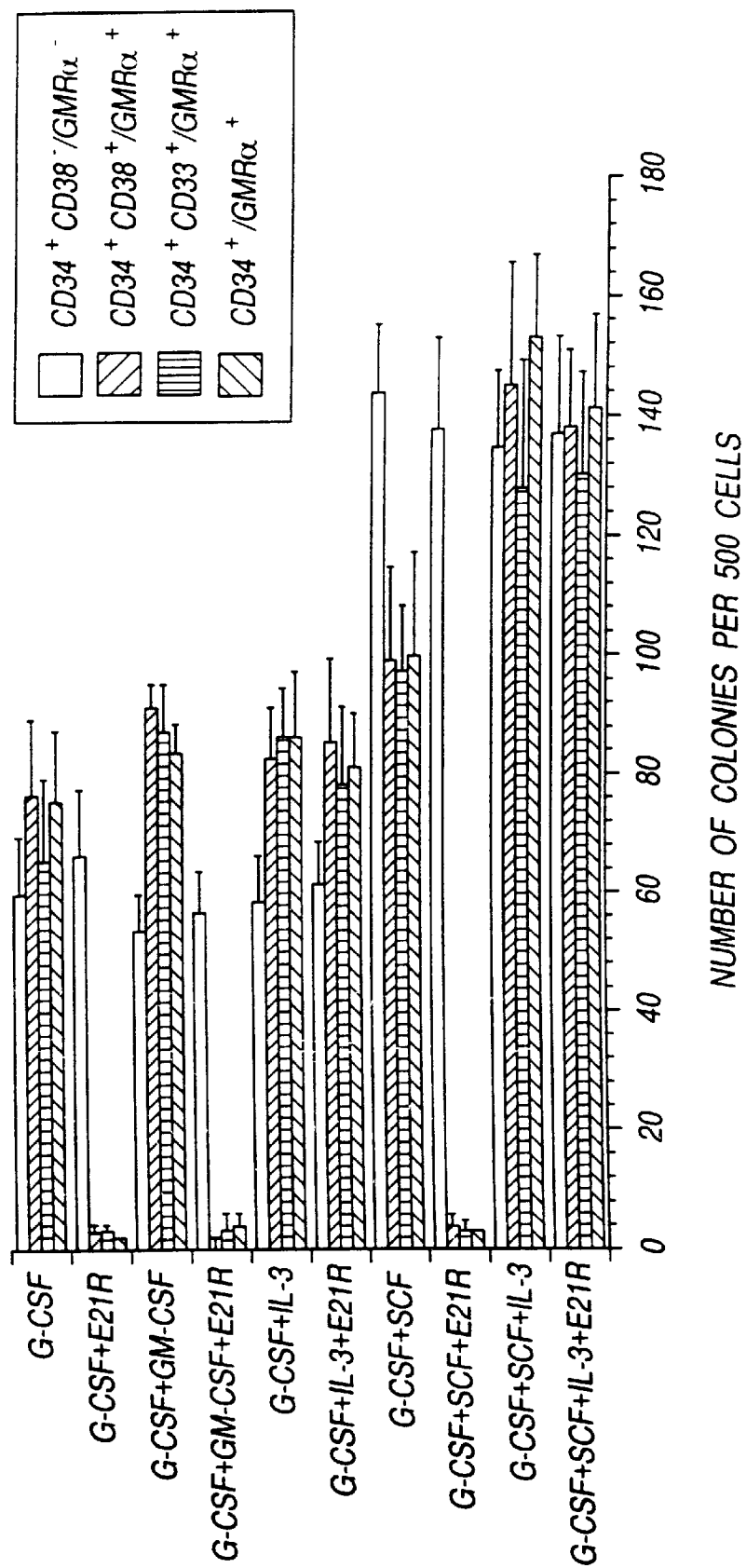

The influence of E21R on growth of the progenitors was further determined in a colony assay. Various combinations of E21R and G-CSF with or without GM-CSF and SCF virtually abolished colony growth, while adding IL-3 overcame the inhibition of colony growth by E21R (FIG. 11d), consistent with E21R inducing apoptosis of committed progenitors (FIG. 11c vs. 11d). It is important to note that CD34$^+$CD38$^-$ cells are non-committed multipotential progenitors. The E21R-induced apoptosis of committed progenitors (CD34$^+$CD38$^+$, CD34$^+$CD33$^+$), but not of CD34$^+$ CD38$^-$ cells will be useful for enrichment of uncommitted progenitors for stem cell transplantation and gene transfer purposes. FIG. 13 shows that the membrane proximal domains of both receptor chains is important for inducing apoptosis.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

---

---

What is claimed is:

1. A method for inducing apoptosis of a cell that comprises the α-chain of the granulocyte macrophage colony stimulating factor (GM-CSF) receptor, said method comprising the step of:
   contacting said cells with an effective amount of a modified GM-CSF polypeptide for a time and under conditions sufficient to induce apoptosis wherein said modified GM-CSF polypeptide comprises a mutation of the glutamate at position 21 of the amino acid sequence of wild-type native GM-CSF to an amino acid selected from the group consisting of: arginine, lysine, glutamine, and as 2. The method according to claim 1 wherein the modified GM-CSF binds to the α-chain of the GM-CSF receptor.

3. The method according to claim 1 wherein the modified GM-CSF polypeptide comprises the substitution of the glutamate at position 21 of the amino acid sequence of wild-type GM-CSF for glutamine in said modified GM-CSF.

4. The method according to claim 1 wherein the modified GM-CSF polypeptide comprises the substitution of the glutamate at position 21 of the amino acid sequence of wild-type GM-CSF for lysine in said modified GM-CSF.

5. The method according to claim 1 wherein the modified GM-CSF polypeptide comprises the substitution of the glutamate at position 21 of the amino acid sequence of wild-type GM-CSF for arginine in said modified GM-CSF.

6. The method according to claim 1 wherein the cells in which apoptosis is induced are normal or malignant myeloid cells.

7. The method according to claim 6 wherein the myeloid cells are myeloid leukemia cells.

8. The method according to claim 1 wherein the modified GM-CSF polypeptide comprises the substitution of the glutamate at position 21 of the amino acid sequence of wild-type GM-CSF for asparagine in said modified GM-CSF.

9. A method for treating myeloid leukemia cells in a human subject wherein said cells comprise the α-chain of the granulocyte macrophage colony stimulating factor (GM-CSF) receptor, said method comprising the step of:
    administering to said human subject an effective amount of a modified GM-CSF polypeptide for a time and under conditions sufficient to directly induce apoptosis wherein said modified GM-CSF polypeptide comprises a mutation of the glutamate at position 21 of the amino acid sequence of wild-type GM-CSF to an amino acid selected from the group consisting of: arginine, lysine, glutamine, and asparagine.

10. The method according to claim 9 wherein the modified GM-CSF binds to the α-chain of the GM-CSF receptor.

11. The method according to claim 9 wherein the modified GM-CSF polypeptide comprises the substitution of the glutamate at position 21 of the amino acid sequence of wild-type GM-CSF for glutamine in said modified GM-CSF.

12. The method according to claim 11 wherein the modified GM-CSF polypeptide comprises the substitution of the glutamate at position 21 of the amino acid sequence of wild-type GM-CSF for lysine in said modified GM-CSF.

13. The method according to claim 12 wherein the modified GM-CSF polypeptide comprises the substitution of the glutamate at position 21 of the amino acid sequence of wild-type GM-CSF for arginine in said modified GM-CSF.

14. The method according to claim 9 wherein the modified GM-CSF polypeptide comprises the substitution of the glutamate at position 21 of the amino acid sequence of wild-type GM-CSF for asparagine in said modified GM-CSF.

15. The method according to claim 1 wherein the cells in which apoptosis is induced are normal or malignant myeloid cells.

16. The method according to claim 6 wherein the myeloid cells are myeloid leukemia cells.

17. A method for selecting bone marrow cells lacking the α-chain of the granulocyte macrophage colony stimulating factor (GM-CSF) receptor, said method comprising:
    (i) contacting said bone marrow cells with an effective amount of a modified GM-CSF polypeptide for a time and under conditions sufficient to induce apoptosis of cells expressing the α-chain of the GM-CSF receptor, wherein said modified GM-CSF polypeptide comprises a mutation of the glutamate at position 21 of the amino acid sequence of wild-type GM-CSF for arginine in said modified GM-CSF; and
    (ii) selecting cells that do not undergo apoptosis, said cells lacking said the α-chain of the GM-CSF receptor.

* * * * *

SEQUENCE LISTING

<160> NUMBER OF SEQ ID NOS: 3

<210> SEQ ID NO 1
<211> LENGTH: 47
<212> TYPE: DNA
<213> ORGANISM: Artificial Sequence
<220> FEATURE:
<223> OTHER INFORMATION: PCR Primer for cloning of E21R protein.

<400> SEQUENCE: 1
tatgttcgct acttcaagct ctacggggaa cgatatcgct gcagcca          47

<210> SEQ ID NO 2
<211> LENGTH: 49
<212> TYPE: DNA
<213> ORGANISM: Artificial Sequence
<220> FEATURE:
<223> OTHER INFORMATION: PCR primer for cloning of E21R protein.

<400> SEQUENCE: 2
agcttggctg cagcgatatc gttccccgta gagcttgaag tagcgaaca          49

<210> SEQ ID NO 3
<211> LENGTH: 12
<212> TYPE: PRT
<213> ORGANISM: Artificial Sequence
<220> FEATURE:
<223> OTHER INFORMATION: Leader Sequence.

<400> SEQUENCE: 3

Met Phe Ala Thr Ser Ser Ser Thr Gly Asn Asp Gly
 1               5                  10